(12) United States Patent
Andreiko

(10) Patent No.: US 9,529,970 B2
(45) Date of Patent: Dec. 27, 2016

(54) SOFTWARE AND METHODS FOR DENTAL TREATMENT PLANNING

(75) Inventor: Craig A. Andreiko, Alta Loma, CA (US)

(73) Assignee: Ormco Corporation, Orange, CA (US)

( * ) Notice: Subject to any disclaimer, the term of this patent is extended or adjusted under 35 U.S.C. 154(b) by 1619 days.

(21) Appl. No.: 12/280,915

(22) PCT Filed: Feb. 28, 2007

(86) PCT No.: PCT/US2007/062965
§ 371 (c)(1),
(2), (4) Date: Dec. 22, 2008

(87) PCT Pub. No.: WO2007/101245
PCT Pub. Date: Sep. 7, 2007

(65) Prior Publication Data
US 2009/0098502 A1   Apr. 16, 2009

Related U.S. Application Data

(60) Provisional application No. 60/777,483, filed on Feb. 28, 2006.

(51) Int. Cl.
*A61C 3/00* (2006.01)
*G06F 19/00* (2011.01)
*A61C 7/00* (2006.01)

(52) U.S. Cl.
CPC ........... *G06F 19/3406* (2013.01); *A61C 7/002* (2013.01)

(58) Field of Classification Search
CPC  A61C 7/002; A61C 2007/002; G06F 19/3406
(Continued)

(56) References Cited

U.S. PATENT DOCUMENTS

| 3,660,900 A | 5/1972 | Andrews |
| 3,860,803 A | 1/1975 | Levine |

(Continued)

FOREIGN PATENT DOCUMENTS

| WO | 97/03622 A1 | 2/1997 |
| WO | 98/58596 A1 | 12/1998 |

(Continued)

OTHER PUBLICATIONS

K. Yamamoto et al., "Optical measurement of dental cast profile and application to analysis of three-dimensional tooth movement in orthodontics," Frontiers of Medical and Biological Engineering, vol. 1, No. 2, pp. 119-130 (1988).

(Continued)

*Primary Examiner* — Heidi M Eide
(74) *Attorney, Agent, or Firm* — Wood Herron & Evans LLP

(57) ABSTRACT

Computer-implemented methods to plan, display and evaluate orthodontic treatment plans. A plurality of teeth in a representation on a computer display may be moved simultaneously in accordance with a mathematically defined pattern. Software tools available to generate the treatment path may include adjusting the smile teeth, moving teeth along a curve fit to points in the mandible, individually moving a tooth, cross sectioning to check for interference and simulations of occlusal points, highlighting teeth that have moved from their original position, making notations on the teeth, and generating and saving animation sequences of before and after treatment tooth positions.

29 Claims, 33 Drawing Sheets

(58) Field of Classification Search
USPC .............. 433/24, 215; 700/95, 98; 703/11
See application file for complete search history.

(56) References Cited

U.S. PATENT DOCUMENTS

| | | | |
|---|---|---|---|
| 4,755,139 A | 7/1988 | Abbatte et al. | |
| 4,798,534 A | 1/1989 | Breads | |
| 4,856,991 A | 8/1989 | Breads et al. | |
| 4,936,862 A | 6/1990 | Walker et al. | |
| 5,011,405 A | 4/1991 | Lemchen | |
| 5,035,613 A | 7/1991 | Breads et al. | |
| 5,055,039 A | 10/1991 | Abbatte et al. | |
| 5,059,118 A | 10/1991 | Breads et al. | |
| 5,131,844 A | 7/1992 | Marinaccio et al. | |
| 5,139,419 A | 8/1992 | Andreiko et al. | |
| 5,186,623 A | 2/1993 | Breads et al. | |
| 5,273,429 A | 12/1993 | Rekow et al. | |
| 5,338,198 A | 8/1994 | Wu et al. | |
| 5,340,309 A | 8/1994 | Robertson | |
| 5,342,202 A | 8/1994 | Deshayes | |
| 5,368,478 A | 11/1994 | Andreiko et al. | |
| 5,382,164 A | 1/1995 | Stern | |
| 5,395,238 A | 3/1995 | Andreiko et al. | |
| 5,431,562 A | 7/1995 | Andreiko et al. | |
| 5,447,432 A | 9/1995 | Andreiko et al. | |
| 5,452,219 A | 9/1995 | Dehoff et al. | |
| 5,454,717 A | 10/1995 | Andreiko et al. | |
| 5,474,448 A | 12/1995 | Andreiko et al. | |
| 5,533,895 A | 7/1996 | Andreiko et al. | |
| 5,549,476 A | 8/1996 | Stern | |
| 5,587,912 A | 12/1996 | Andersson et al. | |
| 5,605,459 A | 2/1997 | Kuroda et al. | |
| 5,607,305 A | 3/1997 | Andersson et al. | |
| 5,645,421 A | 7/1997 | Slootsky | |
| 5,975,893 A | 11/1999 | Chishti et al. | |
| 6,015,289 A | 1/2000 | Andreiko et al. | |
| 6,227,850 B1 | 5/2001 | Chishti et al. | |
| 6,244,861 B1 | 6/2001 | Andreiko et al. | |
| 6,471,512 B1 | 10/2002 | Sachdeva et al. | |
| 6,575,751 B1 | 6/2003 | Lehmann et al. | |
| 6,616,444 B2 | 9/2003 | Andreiko et al. | |
| 2001/0002310 A1 | 5/2001 | Chishti et al. | |
| 2002/0028417 A1 | 3/2002 | Chapoulaud et al. | |
| 2004/0029068 A1* | 2/2004 | Sachdeva et al. | 433/24 |
| 2004/0073417 A1* | 4/2004 | Rubbert et al. | 703/11 |
| 2004/0096799 A1* | 5/2004 | Hughes et al. | 433/24 |
| 2004/0197727 A1* | 10/2004 | Sachdeva et al. | 433/24 |
| 2005/0123175 A1* | 6/2005 | Werthiem et al. | 382/124 |
| 2005/0208449 A1* | 9/2005 | Abolfathi et al. | 433/24 |
| 2006/0275731 A1* | 12/2006 | Wen et al. | 433/24 |

FOREIGN PATENT DOCUMENTS

| | | |
|---|---|---|
| WO | 01/47405 A2 | 7/2001 |
| WO | 2004/028391 A2 | 4/2004 |

OTHER PUBLICATIONS

P.R. Crawford, "CAD/CAM in the dental office: does it work?" Journal, vol. 57, No. 2, pp. 121-123, Feb. 1991.

R.H. Biggerstaff, "Computerized diagnostic setups and simulations," The Angle Orthodontist, vol. 40, No. 1, pp. 28-36, Jan. 1970.

* cited by examiner

SOFTWARE AND METHODS FOR DENTAL TREATMENT PLANNING

CROSS REFERENCE TO RELATED APPLICATIONS

This application claims the benefit of the PCT Application PCT/US2007/062965, filed on 28 Feb. 2007, entitled "SOFTWARE AND METHODS FOR DENTAL TREATMENT PLANNING," which is herby incorporated in its entirety by reference herein, which claims the benefit of U.S. Provisional Application Ser. No. 60/777,483, filed 28 Feb. 2006, and entitled "SOFTWARE AND METHODS FOR DENTAL TREATMENT PLANNING," which is hereby incorporated in its entirety by reference herein.

FIELD OF THE INVENTION

The invention relates generally to the field of orthodontics and, more particularly, to computer-automated development of an orthodontic treatment plan and appliance.

BACKGROUND OF THE INVENTION

The orthodontic treatment of patients has as its fundamental objective the repositioning or realignment of the teeth of a patient in the patient's mouth to positions where they function optimally together and occupy relative locations and orientations that define a pair of opposed and cooperating planar, or nearly planar, smooth arches. The teeth of the two arches, the maxillary arch of the teeth of the upper jaw and the mandibular arch of the teeth of the lower jaw, when in optimal or ideal positions, contact the teeth of the opposite arch along a surface that is usually flat or slightly upwardly concave and commonly referred to as the plane of occlusion.

The treatment applied to patients who have been diagnosed as having teeth insufficiently close to the ideal positions to require orthodontic correction includes an initial or rough procedure to overcome the more serious defects of tooth positioning followed by a finish treatment designed to bring the teeth as closely as possible or practical to their ideal positions. The rough treatment usually involves the movement of certain teeth through the use of any of a number of recognized techniques performed by an orthodontist, and sometimes procedures such as the extraction of certain teeth or surgery on the patient's jaw performed by an oral surgeon.

In the finish treatment, the orthodontist applies an appliance to the teeth of the patient to exert continual forces on the teeth of the patient to gradually urge them toward their ideal positions, lire most common, but not the only, type of appliance is a set of braces made up of brackets and arch wires. The application of this type of appliance usually involves the attachment of brackets to the teeth, either with the application of adhesive to the teeth or the securing of bands around the teeth. The brackets are usually each provided with a slot through which an arch wire is extended. One arch wire is provided for the upper teeth and one for tire lower teeth. Typically, the slots in the brackets are of rectangular cross-section and the arch wire is of rectangular cross-section. The arch wire installed in the slots of the brackets interconnects the teeth, through the brackets, and exerts forces on the teeth to translate or rotate them toward a finish position envisioned by the orthodontist.

In dental procedures in general and more specifically in orthodontic procedures, a model of a patient's teeth is required in order to make treatment decisions in, for example, design of braces, crowns, bridges, etc., and to allow monitoring of dental procedures. Of particular importance is knowledge of the distance and spatial relationship between the teeth on opposite jaws.

Dental procedures requiring knowledge of the position of teeth and the distance between teeth on opposite jaws, generally use models of the teeth, referred to hereinafter as "dental models". Typically, plaster dental models are used, which are made by casting plaster into the negative impression made by teeth in an appropriate matrix. Dental models can, however, be made of any convenient material.

This approach, however, has a number of major drawbacks. First, in the occluded state it is difficult to see the relation between facing surfaces of opposite teeth of the upper and lower jaws. Second, on moving a tooth, or adding a tooth, or changing the form of a tooth in the dental model, it is not easy to see if the affected tooth affects the occlusion. Third, the information provided by dental models regarding proximity of opposite teeth in opposite jaws is typically no more than whether certain points of opposite teeth make contact, or not, in the occluded state. In order to be able to arrive at an optimal closing of the teeth when changes are made to one or more of the teeth of the dental model, a fairly long and tiresome process of physically modeling the affected teeth is required in order to ensure a good fit between opposite teeth on opposite jaws in the occluded state.

It has been recognized in the design and application of orthodontic appliances that an ideally designed and installed orthodontic appliance will, for example, present the slots of the brackets in a position to initially receive a pre-shaped arch wire that will elastically deform to exert corrective forces on the teeth to urge them toward their finish positions. When in their finish positions, the arch wire of the ideally designed appliance will no longer be elastically deformed, and will no longer exert forces upon the teeth. Achieving this objective has been inhibited by certain problems in the prior art.

One problem presented by the prior art is that current orthodontic products are designed and manufactured to average anatomy. As a result, orthodontists are faced with the need to select what they perceive to be the brackets and arch wires of the closest design to those required by a particular patient, and to modify the designs for treatment of the patient. Some of this modification may be performed when the appliance is initially installed, but almost inevitably modification is required during the course of treatment of the patient. This modification may lake the form of the replacement of brackets, but most commonly requires a periodic bending and reshaping of the arch wire as the treatment progresses. Thus, the treatment of the patient has become a manual feedback system in which the orthodontist monitors the progress of the patient's treatment and then readjusts the appliance, usually by bending the arch wires, to correct the forces being applied to the teeth to bring the teeth to their ultimate positions, which are less than ideal. As a result, the patient may be subjected to treatment over a period that is longer than would be necessary if the appliance were initially made to the optimum design. In addition, the time required of the orthodontist for implementation of the treatment may be several times greater than it would be if modification of the appliance were unnecessary. Thus, the orthodontist is able to treat fewer patients and the cost of the treatment to the patient or to the orthodontist is increased.

Location of the connection points for the appliance to the teeth also presents a problem in the prior art. Typically, brackets are bonded to the teeth and then interconnected by the installation of the arch wires. This is done when the teeth are in their maloccluded positions, with the orthodontist having only a mental vision of where the finish positions of the teeth will be and where the brackets are to be placed to move the teeth to those finish positions. For more effective use of the appliance and to promote ease in cleaning the teeth, the orthodontist prefers to locate the brackets and arch wires away from the gums. If they are placed to close to the tips of the teeth, however, they may interfere with the teeth of the opposite arch as the teeth approach their finish positions.

Another problem of the prior art that has inhibited the selection or design of an ideal orthodontic appliance for the patient is the difficulty in arriving at an expression of the ideal finish position of the teeth. Orthodontists typically make models of the patient's mouth and, with the models and the aid of x-rays, determine a treatment to move the teeth to finish tooth positions. This process is time consuming and presents a source of error and inaccuracy. From the measurements and based on the judgment of the orthodontist, appliance components are selected to implement the prescribed treatment. In reality, the treatment of patients is in many cases more of an art than a science, with results ranging from, poor to excellent, and generally variable.

The need for custom manufactured orthodontic appliances and the use of automatic design techniques has been recognized by some, while others have advocated adherence to standard components and manual techniques in view of a perceived lack of practical custom appliance manufacturing and automated appliance design systems of the art.

The development of automated custom appliance design systems has encountered several difficulties. These difficulties have included the task of developing an automated system that includes reliable and efficient decision making algorithms and techniques for automatically determining an ideal finish position of the teeth. Further, these difficulties have included arriving at an expression of appliance geometry in terms that can be efficiently produced by automated appliance manufacturing equipment. Furthermore, the prior art has not provided a way to accurately manufacture an appliance on an individualized basis in accordance with the appliance design. An additional problem in the automated design and manufacture of orthodontic appliances lies in the difficulty in designing the custom design system to take into account the professionally recognized parameters and criteria, derived over many years from the knowledge and experience of the practicing and clinical orthodontist, upon which diagnosis and treatment is based.

Tooth positioners for finishing orthodontic treatment are described by Kesling in the Am. J. Orthod. Oral. Surg. 31:297-304 (1945) and 32:285-293 (1946). The use of silicone positioners for the comprehensive orthodontic realignment of a patient's teeth is described in Warunek et al. (1989) J. Clin. Orthod. 23:694-700. Clear plastic retainers for finishing and maintaining tooth positions are commercially available from Raintree Essix, Inc., New Orleans, La. 70125, and Tru-Tain Plastics, Rochester, Minn. 55902. The manufacture of orthodontic positioners is described in U.S. Pat. Nos. 5,186,623; 5,059,118; 5,055,039; 5,035,613; 4,856,991; 4,798,534; and 4,755,139.

Other publications describing the fabrication and use of dental positioners include Kleemann and Janssen (1996) J. Clin. Orthodon. 30:673-680; Cureton (1996) J. Clin. Orthodon. 30:390-395; Chiappone (1980) J. Clin. Orthodon. 14:121-133; Shilhday (1971) Am. J. Orthodontics 59:596-599; Wells (1970) Am. J. Orthodontics 58:351-366; and Cottingham (1969) Am. J. Orthodontics 55:23-31.

Kuroda et al. (1996) Am. J. Orthodontics 110:365-369 describes a method for laser scanning a plaster dental cast to produce a digital image of the cast. See also U.S. Pat. No. 5,605,459.

U.S. Pat. Nos. 5,533,895; 5,474,448; 5,454,717; 5,447,432; 5,431,562; 5,395,238; 5,368,478; and 5,139,419, assigned to Ormco Corporation, describe methods for manipulating digital images of teeth for designing orthodontic appliances.

U.S. Pat. No. 5,011,405 describes a method for digitally imaging a tooth and determining optimum bracket positioning for orthodontic treatment. Laser scanning of a molded tooth to produce a three-dimensional model is described in U.S. Pat. No. 5,338,198. U.S. Pat. No. 5,452,219 describes a method for laser scanning a tooth model and milling a tooth mold. Digital computer manipulation of tooth contours is described in U.S. Pat. Nos. 5,607,305 and 5,587,912. Computerized digital imaging of the jaw is described in U.S. Pat. Nos. 5,342,202 and 5,340,309. Other patents of interest include U.S. Pat. Nos. 5,549,476; 5,382,164; 5,273,429; 4,936,862; 3,860,803; 3,660,900; 5,645,421; 5,055,039; 4,798,534; 4,856,991; 5,035,613; 5,059,118; 5,186,623; and 4,755,139.

With the advent of powerful computers and advanced computer aided design techniques, three-dimensional virtual dental models help in alleviating the problems encountered with the plaster dental models. Storing a computer virtual dental model on a computer can be achieved "directly" by scanning and digitizing the teeth and gums, or "indirectly" by utilizing a plaster dental model or the negative impression. The latter method is disclosed in PCT Application No. PCT/IL 96/00036, Publication No. WO 97/03622, published on Feb. 6, 1997, hereinafter incorporated by reference. However, none of the existing virtual computer dental models provide tools relating to the distance between opposite teeth on opposite jaws.

SUMMARY OF THE INVENTION

Certain aspects of the following invention solve these and other problems by providing a software modeling tool capable of manipulating the digital images of the teeth from their original position as digitized and scanned to an optimal position. The tool allows the treating orthodontist to develop a treatment plan based on evaluating tooth movements in the modeling tool.

The software modeling tool assists the orthodontist in manipulating the tooth positions by allowing to orthodontist to adjust the following items. The orthodontist may adjust the positions of the smile teeth, the front four teeth that are most visible when a person smiles by adjusting the teeth along an arc. The orthodontist may adjust the spacing of the teeth in the mandible and their relative positions corresponding to a curve fit through the mandible for optimal tooth placement. The orthodontist may utilize tools that cross section the teeth which allows him/her to check for alignment interferences between the top and bottom teeth. The orthodontist may adjust an individual tooth in six different degrees of freedom to place the tooth in its optimal position or in a position for better movement with other teeth. The orthodontist also has the ability to review a simulated representation of the occlusal points with the teeth in their current and new positions to assist in developing the treatment plan.

The software modeling tool may also assist the orthodontist by allowing him to add notations to teeth as part of the treatment process. The software modeling tool may indicate to the orthodontist, which teeth have moved from their original position. It allows the orthodontist to undo and redo tooth movements as the orthodontist is developing the treatment plan. The software modeling tool allows the orthodontist to create animation sequences of the teeth moving from their original positions to their final positions and save those animations to appropriate files, which may be archived or even given to patients as a marketing tool, by the office to show them the effects of the treatment.

From the foregoing disclosure and the following more detailed description of various preferred embodiments it will be apparent to those skilled in the art that the present invention provides a significant advance in the technology of developing treatment plans for orthodontics. Particularly significant in this regard is the potential the inventor affords for providing the orthodontist to simulate tooth movements and check for proper alignments before a treatment plan is started. Additional features and advantages of various preferred embodiments will be better understood in view of the detailed description provided below.

BRIEF DESCRIPTION OF THE DRAWINGS

These and further features of the present invention will be apparent with reference to the following description and drawings wherein.

DETAILED DESCRIPTION OF CERTAIN PREFERRED EMBODIMENTS

Systems and methods that use computers to model a patient's teeth and to design orthodontic treatment and appliances have been proposed by applicant, examples of which are disclosed in International Applications Nos. PCT/US2003/030917, filed on Sep. 26, 2003, and International Patent Application No. PCT/US00/35558, filed Dec. 29, 2000, both hereby expressly incorporated herein by reference in their entireties. Typical systems of these types provide an interface through which a treating orthodontist or others can communicate treatment and design preferences and data. The present invention provides enhancements to such systems that improve the functionality and utility of such systems, as set forth herein.

Figure 1:
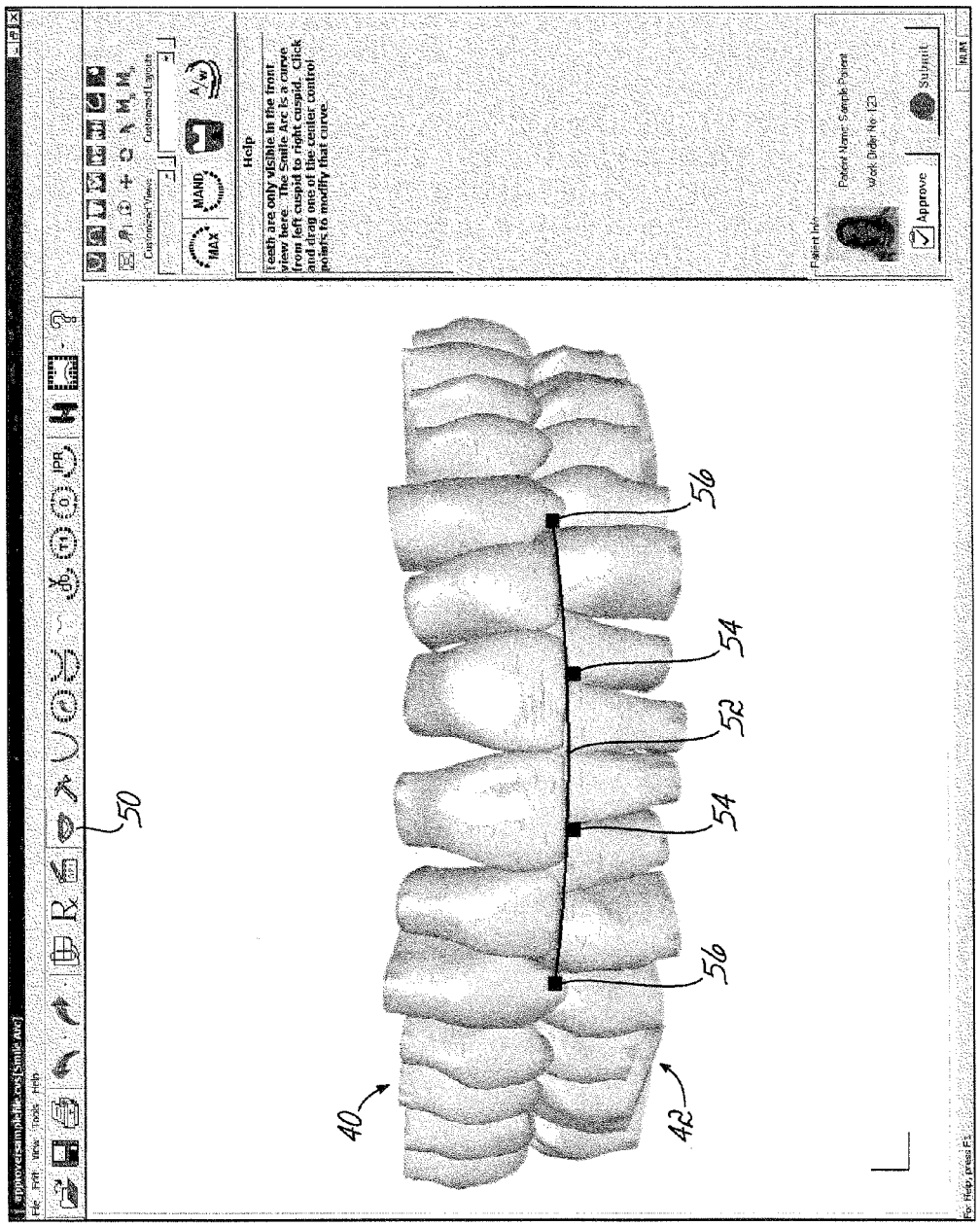
FIG. 1 contains a representative screen shot from the software showing the adjustment of the smile arc.
Figure 2:
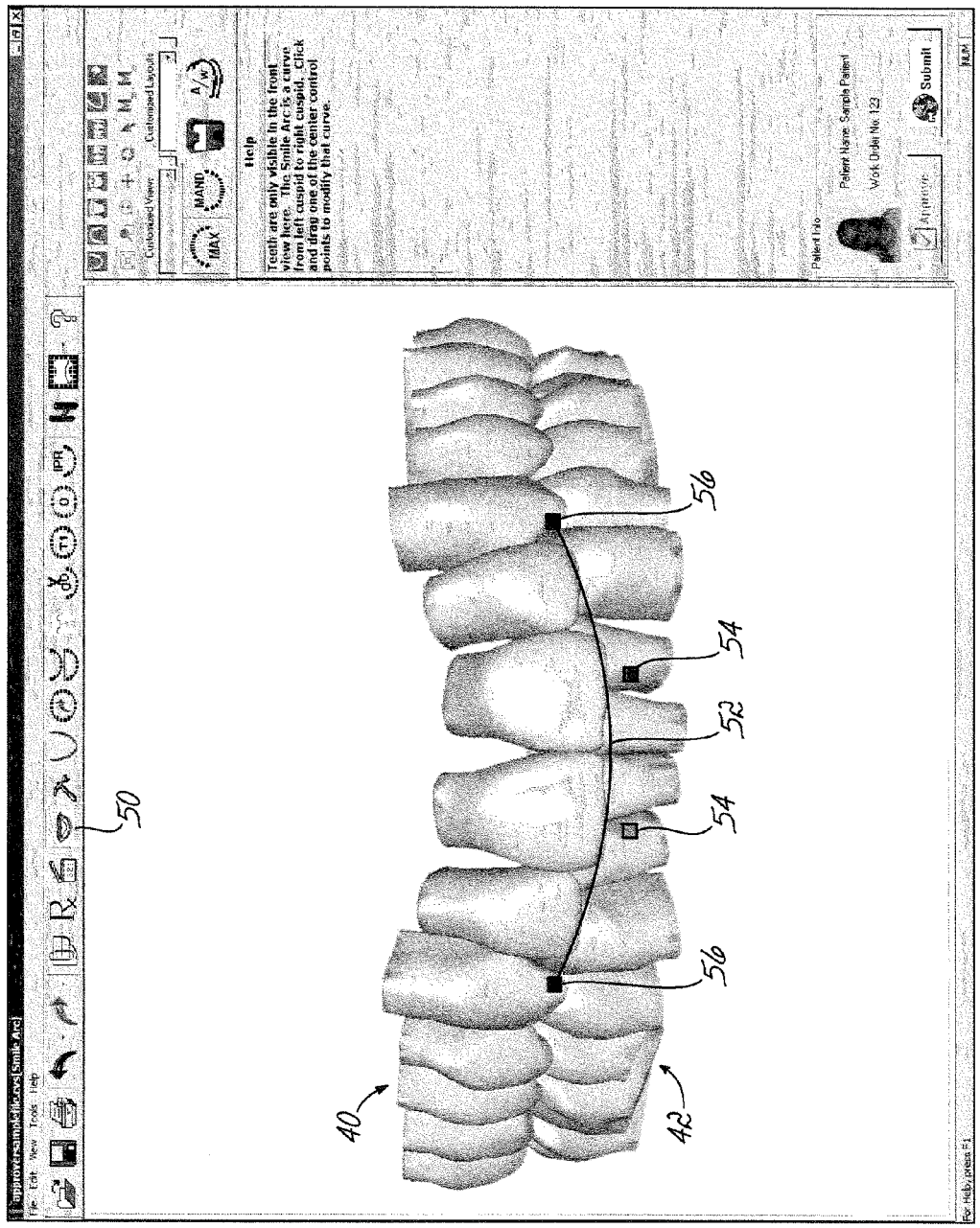
FIG. 2 contains a representative screen shot from the software showing the smile arc adjusted downward.
Figure 3:
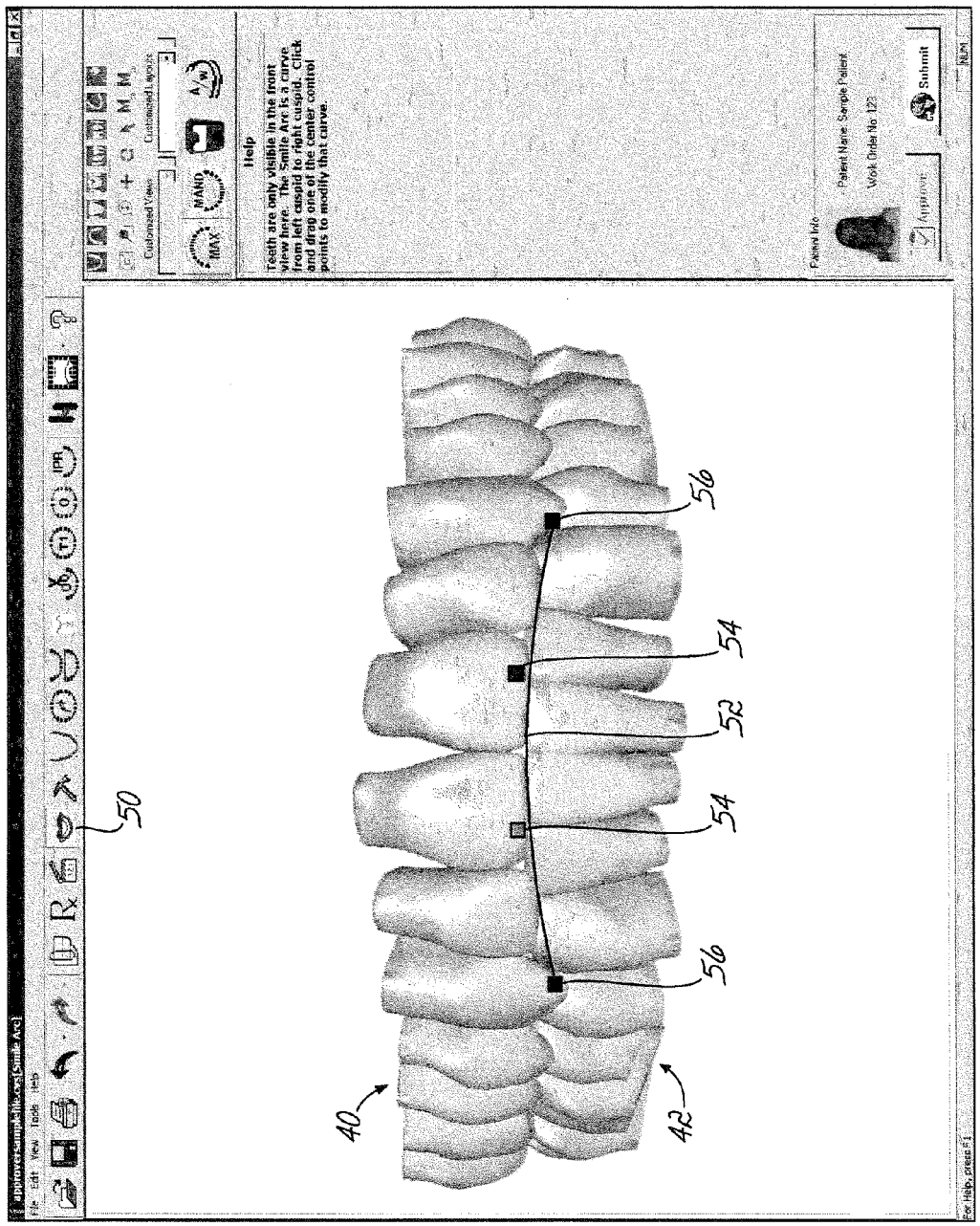
FIG. 3 contains a representative screen shot from the software showing the smile arc adjusted upward.

Traversing the functionality of the software containing the computer implemented method, and referring now to FIGS. 1 through 3, upon picking a Smile Arc icon 50, a user may see both the assemblies (maxillary 40 and mandibular 42) in front view along with a smile arc 52. The smile arc 52 is a symmetric curve interpolated through BC points of maxillary incisors, drawn starting from left cuspid up to right cuspid. Two points on the cuspids 56 are the fixed whereas two intermediate points 54 are flexible and can be moved. When user selects one of the movable control points 54 and drags the control point up/down, modifying the smile arc 52, upper incisors will move up/down with the curve. In/out correction is applied to avoid interference with lower assembly. Anchor points 56 of the smile arc 52 are displayed in a different color.

Only some of the teeth in a person's mouth are visible in a smile. These teeth, referred to as the "smile teeth" primarily consist of the front four upper teeth. Being able to adjust these four teeth along a smooth arc may give the impression of a much better smile without the need to adjust all of the teeth. In order to determine the adjustments to the smile teeth, the software package contains a feature that allows the user to adjust the front four teeth along an arc type path. The adjustment arc is permanently attached to the top left and right cuspids. The adjustment arc, known as the smile arc 52 in the software also contains several control points 54 located between the anchor points 56. These control points 54 allow the user to adjust the smile arc 52 by moving the control points 54 in a vertical direction. As the control points 54 are moved the front four upper teeth move as well following the adjustments to the smile arc 52.

Initially the user would select the Smile Arc icon 50 from the tool bar or from the menu system by selecting Edit and then Smile Arc. To move a control point 54, the user selects the moveable control point 54 on the smile arc 52 with his mouse and while holding down the left mouse button, drags the control point 54, which in turn moves the corresponding teeth, to the new desired location. At that point the user releases the mouse button and the teeth are set in their new location. If further adjustments are necessary, the user would follow the same procedure of selecting one of the control points 54 and then holding down the left mouse button, make the adjustment. Predetermined limits set bounds for the adjustments to the front four teeth.

Figure 4:
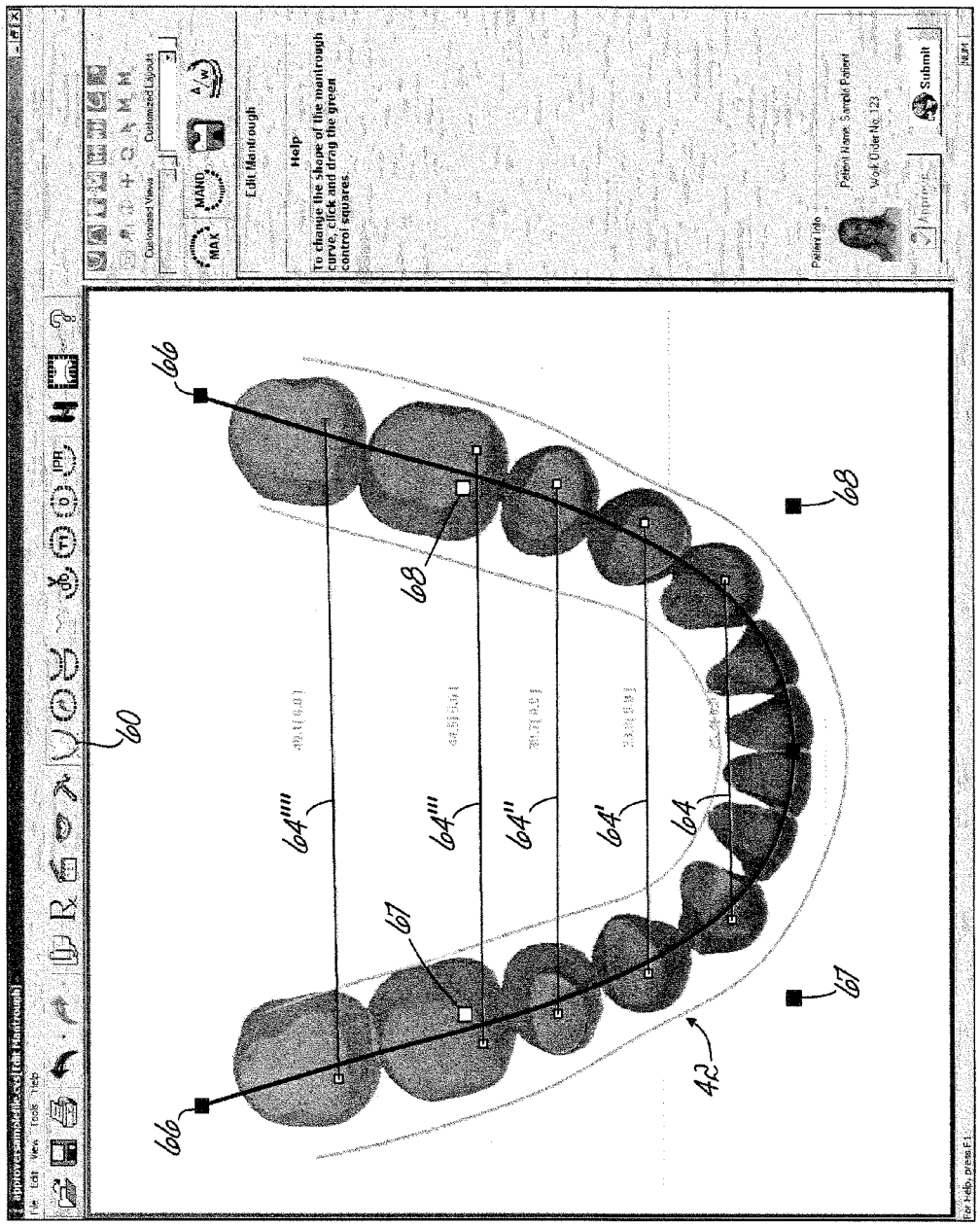
FIG. 4 contains a representative screen shot from the software showing the adjustment of the mantrough.
Figure 5:
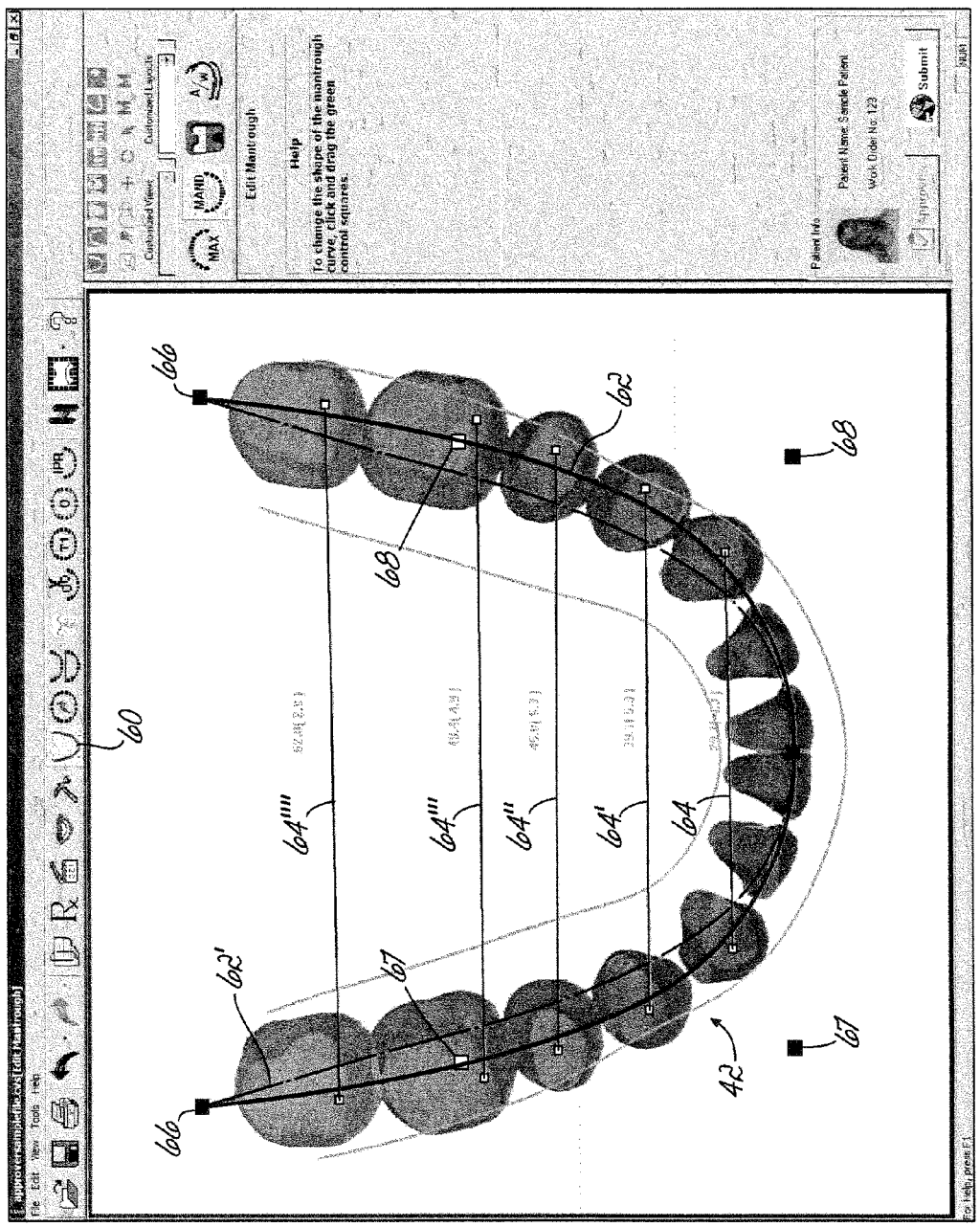
FIG. 5 contains a representative screen shot from the software showing the mantrough adjusted outward.
Figure 6:
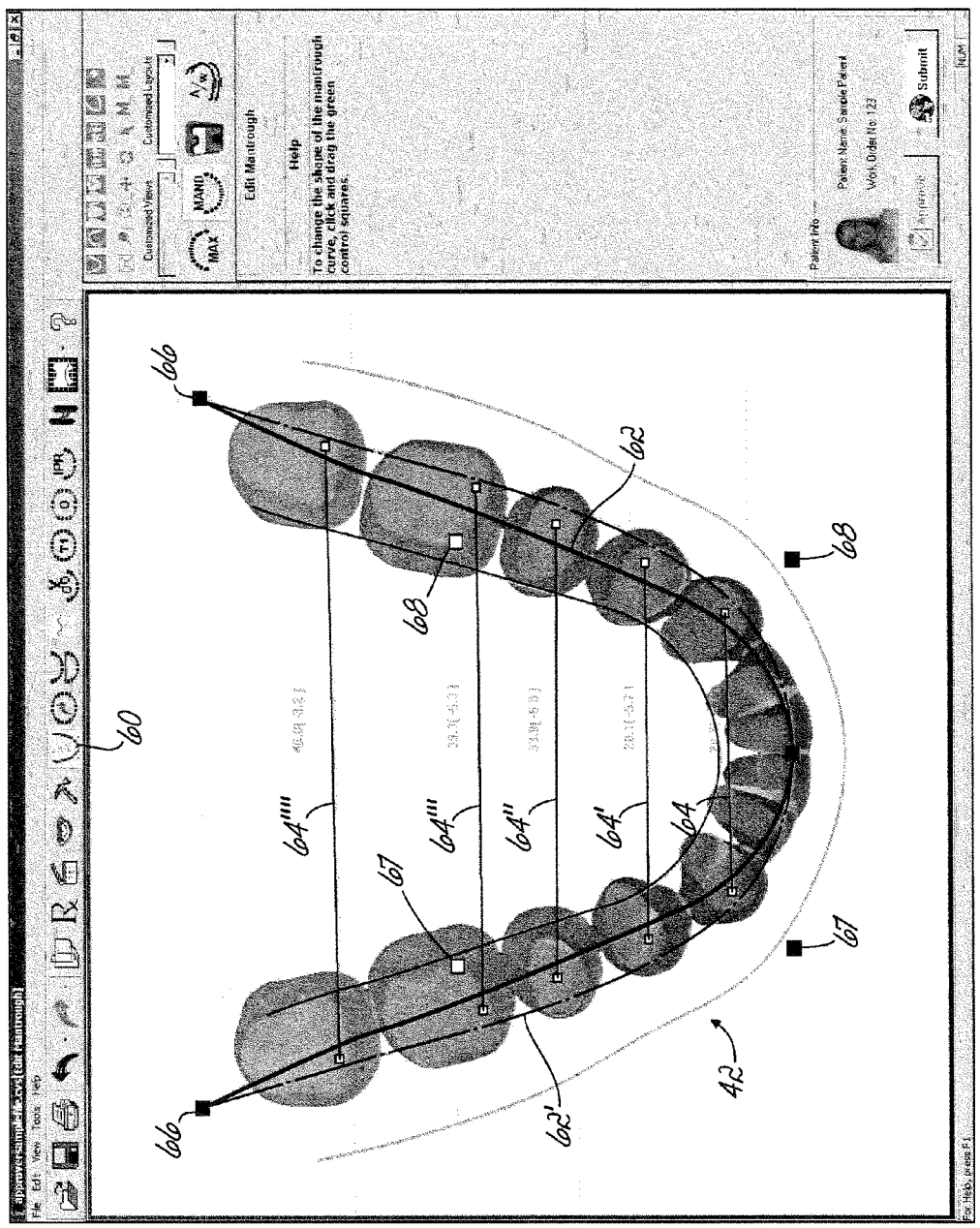
FIG. 6 contains a representative screen shot from the software showing the mantrough adjusted inward.

Referring now to FIGS. 4 through 6, by selecting Edit Mantrough, the display area will become single window. Transparent teeth will be visible along with the mantrough curve. The user can select one of the control points available along the mantrough (a representation of the patient's mandibular trough) and drag it. On dragging the control point, shape of mantrough curve will be modified accordingly and mandibular 42 as well as maxillary 40 teeth will be modified to reflect those changes.

Edit Mantrough shows the distances between BC lines 64. Every BC line will 64 show distance values such as 31.9 (1.3). In this example 31.9 is a. BC distance on setup and the value inside the brackets is a deviation from that initial value.

The Edit Mantrough feature of the software allows the user to change the shape of the mantrough. The method of calculating an orthodontic setup of a patient's teeth includes calculating a symmetrical arch comprising fixing points 66 along the lower incisors to align the lower incisal edges to a best-fit buccal cusp curve that enables placement of upper incisors. This curve is calculated from points at the measured distances on midline to define thereby the origin of an anterior bezier handle, and defining the mesial facial cusps of lower molars as posterior bezier handles. The method of using bezier handles is described in U.S. Pat. Nos. 6,015,289, 6,244,861, and 6,616,444, which are expressly incorporated herein in their entirety by reference.

To change the shape of the mantrough, the user may select the Edit Mantrough icon 60 from the tool bar or from the menu system by selecting Edit and then Edit Mantrough. The teeth 40, 42 and the curve 62 are displayed along with a plurality of tooth-to-tooth distance measurements. The curve 62 is anchored to the two rear most teeth and series of bezier handles, referred to in the software as Control Points 67, 68 or sometimes curvature knots, are available to the user to make adjustments to the curve 62. To adjust the curve 62, the user selects one of the control points 67, 68 with his mouse and while holding down the left mouse button, drags the control point 67, 68 to the new location, thus changing the shape of the curve 62. As the curve 62 changes shape, the teeth 40, 42 automatically follow the curve 62 in real time allowing the user to graphically see how the changes in the shape of the curve 62 affect the placement of the teeth 40, 42.

The control points 67, 68 may be moved in horizontal and/or vertical directions. Preset limits bound the distance that a control point 67, 68 may be moved. As the control points 67, 68 are moved, the updated tooth to tooth lines 64, 64', 64", 64''', 64'''' and distance measurements are displayed along with a the distance that the two teeth have moved relative to their the original position. The original curve 62' is also continuously displayed in an alternate color allowing the user to see the deviations made from the original position as the control points 67, 68 are moved. Control point movement may be set so that corresponding control points 67, 68 follow the same but mirror image of their counterpart being moved in order to make symmetrical adjustments. Alternatively, the control points 67, 68 may be independent of one another for unsymmetrical adjustments.

Figure 7:
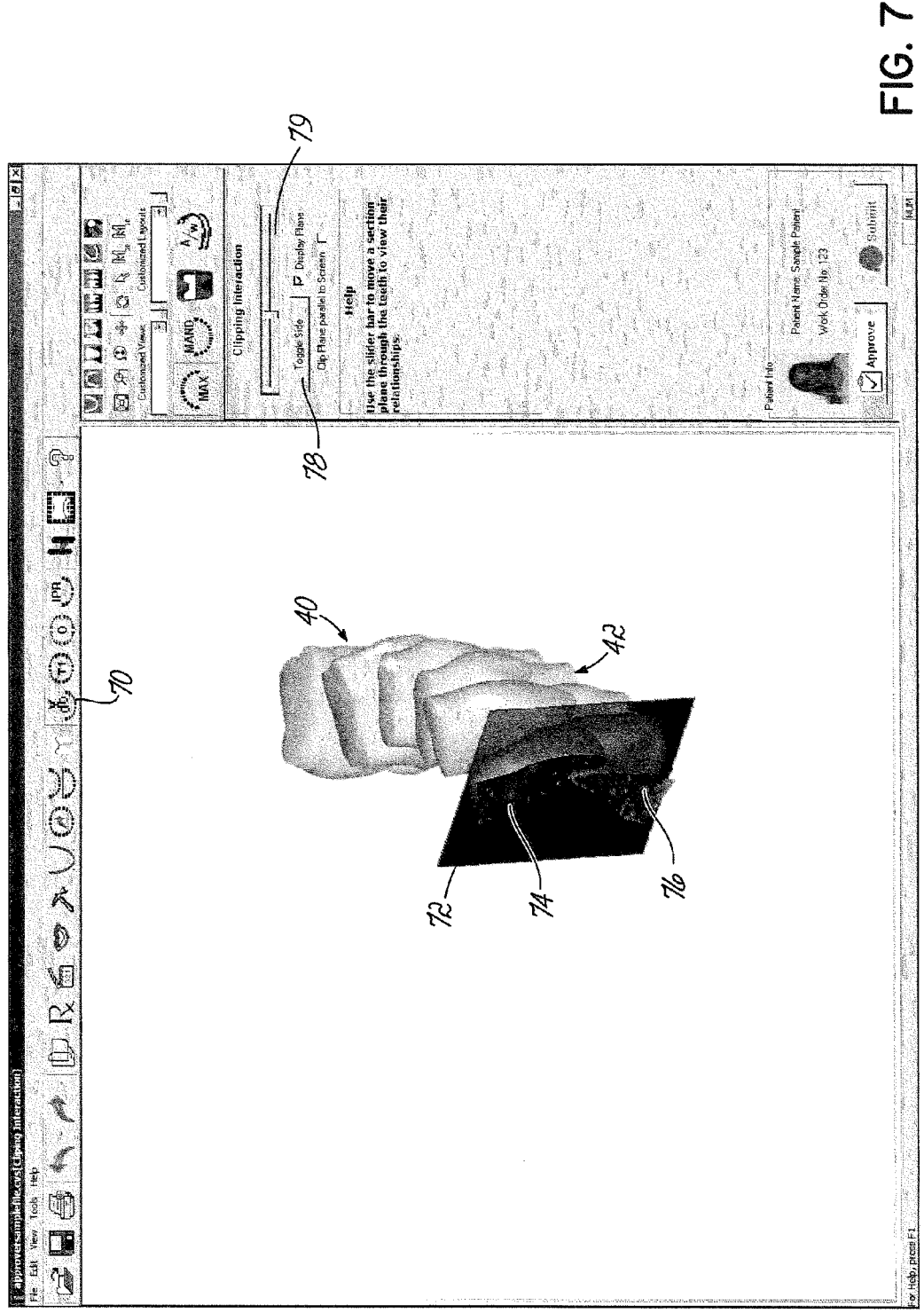
FIG. 7 contains a representative screen shot from the software showing the use of a clipping plane where the plane moves through the teeth.
Figure 8:
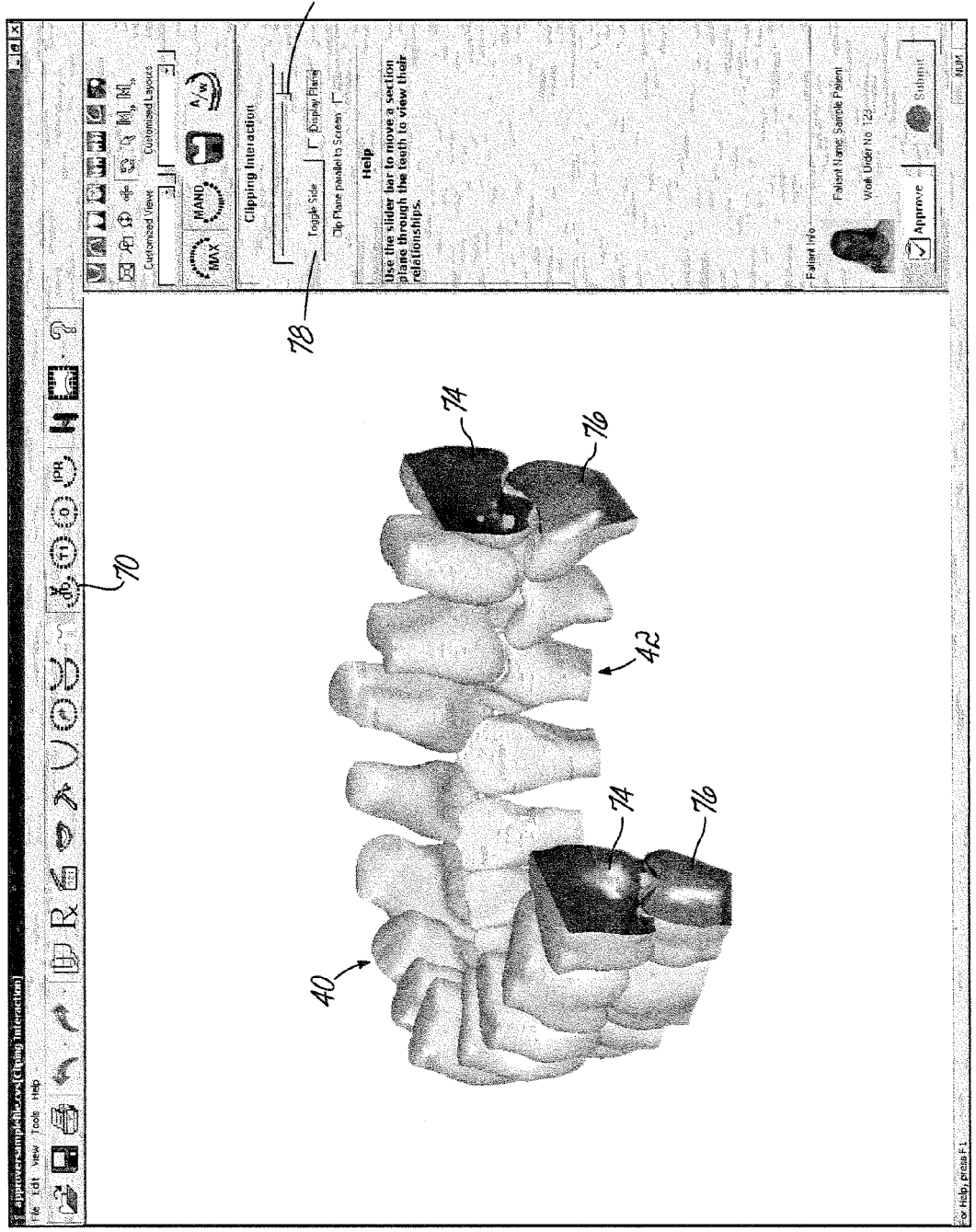
FIG. 8 contains another representative screen shot from the software showing the use of a clipping plane where the plane moves through the teeth.
Figure 9:
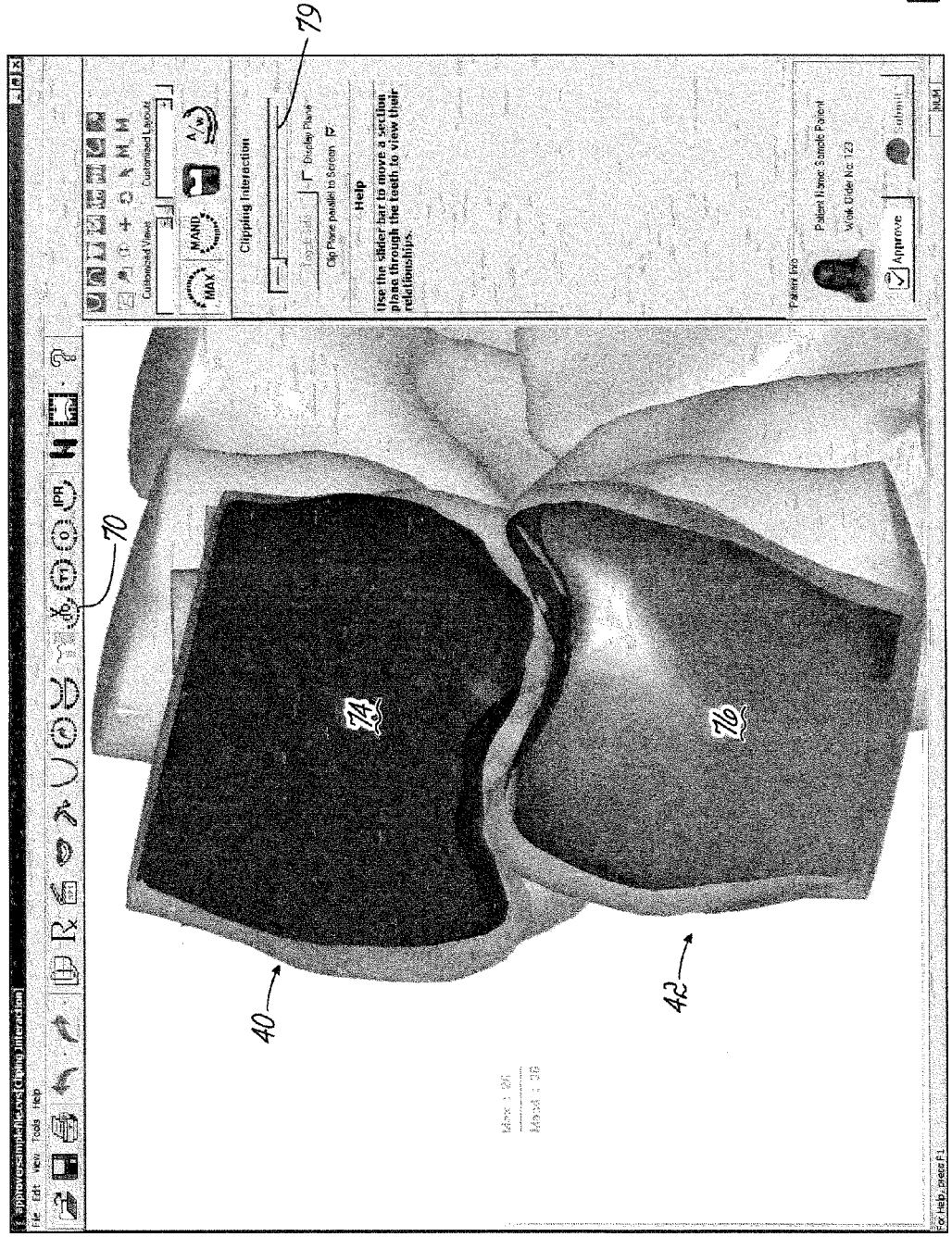
FIG. 9 contains a representative screen shot from the software showing the use of a clipping plane where the plane remains stationary and the teeth move through the plane.
Figure 10:
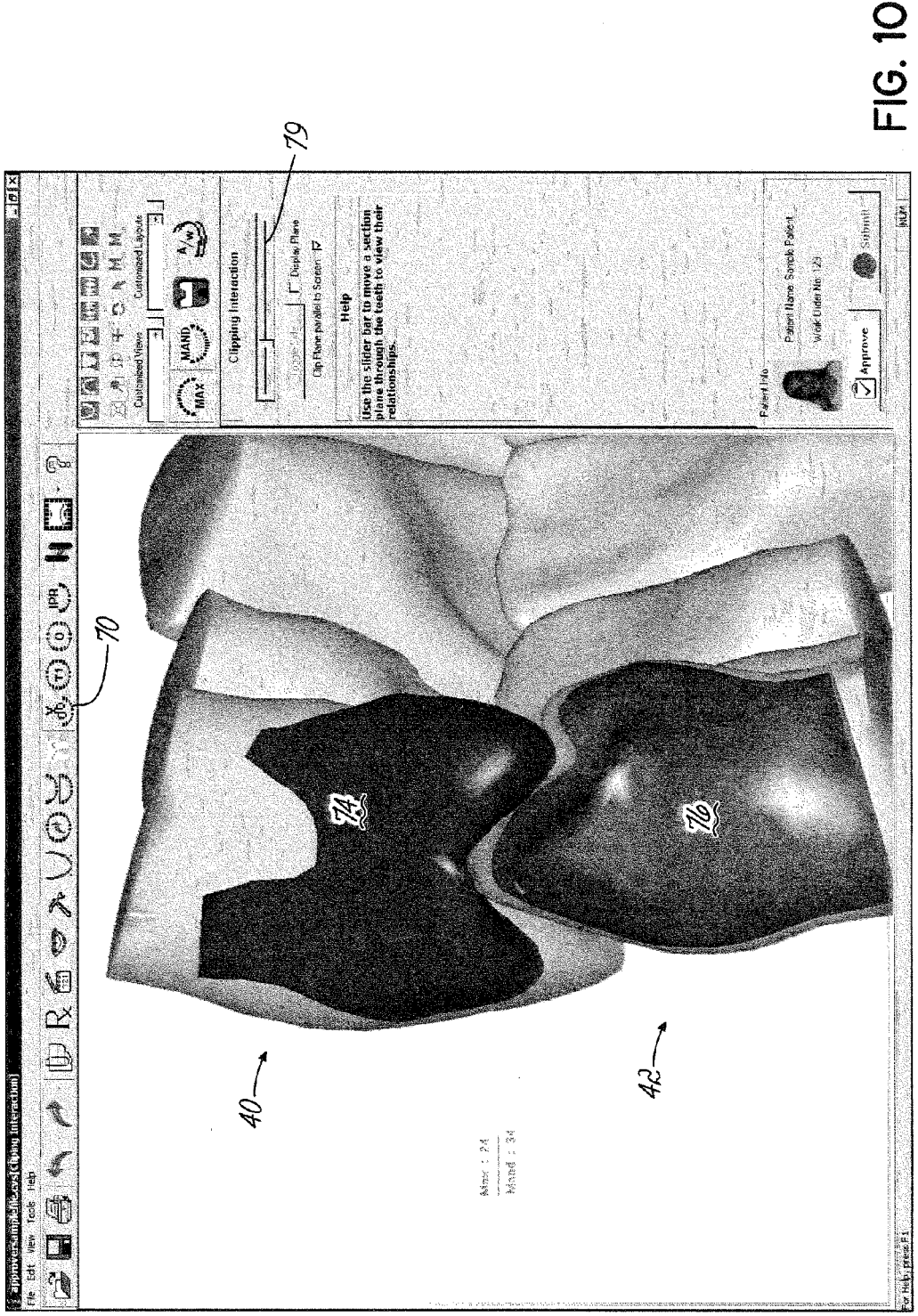
FIG. 10 contains another representative screen shot from the software showing the use of a clipping plane where the plane remains stationary and the teeth move through the plane.
Figure 11:
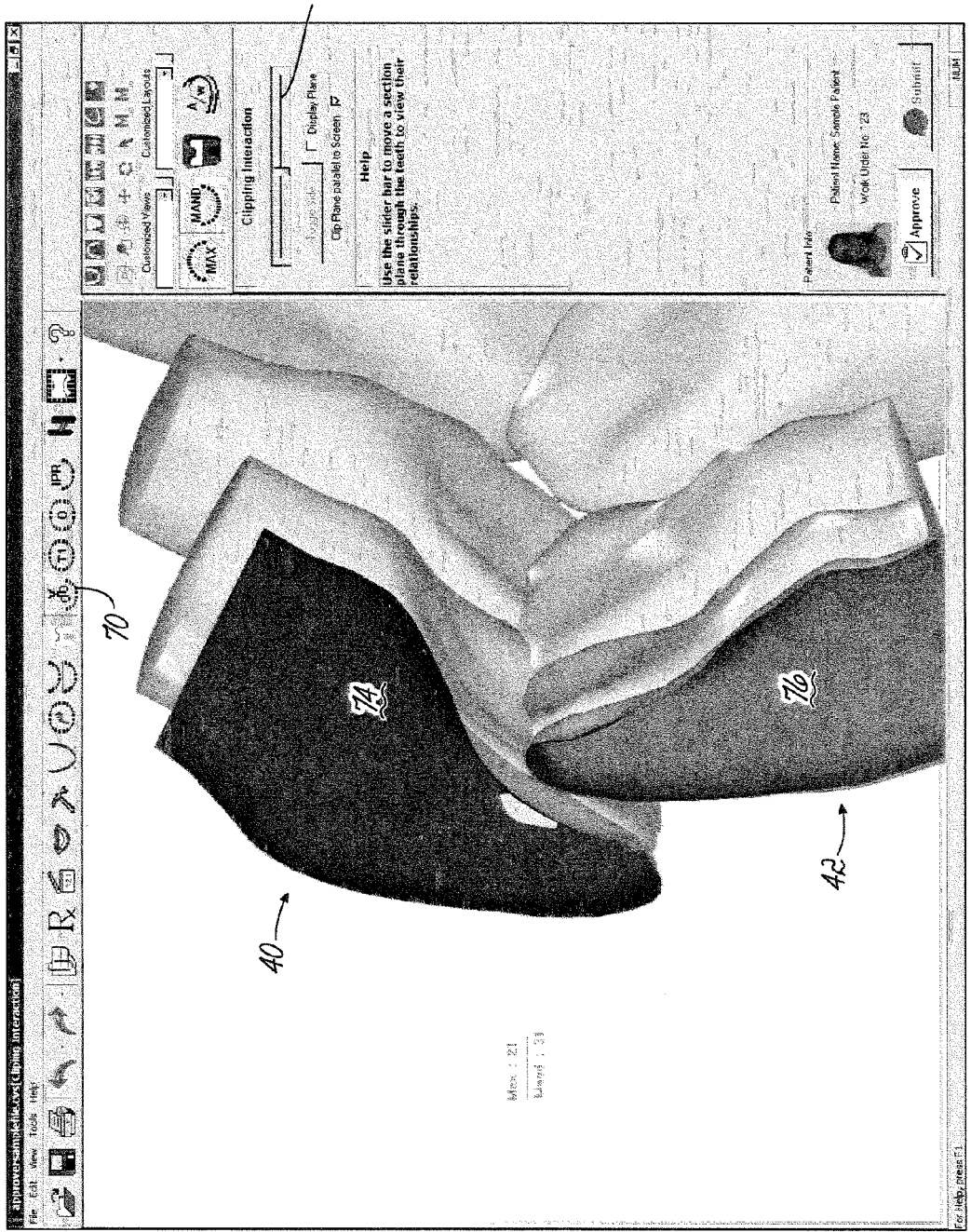
FIG. 11 contains another representative screen shot from the software showing the use of a clipping plane where the plane remains stationary and the teeth move through the plane.
Figure 12:
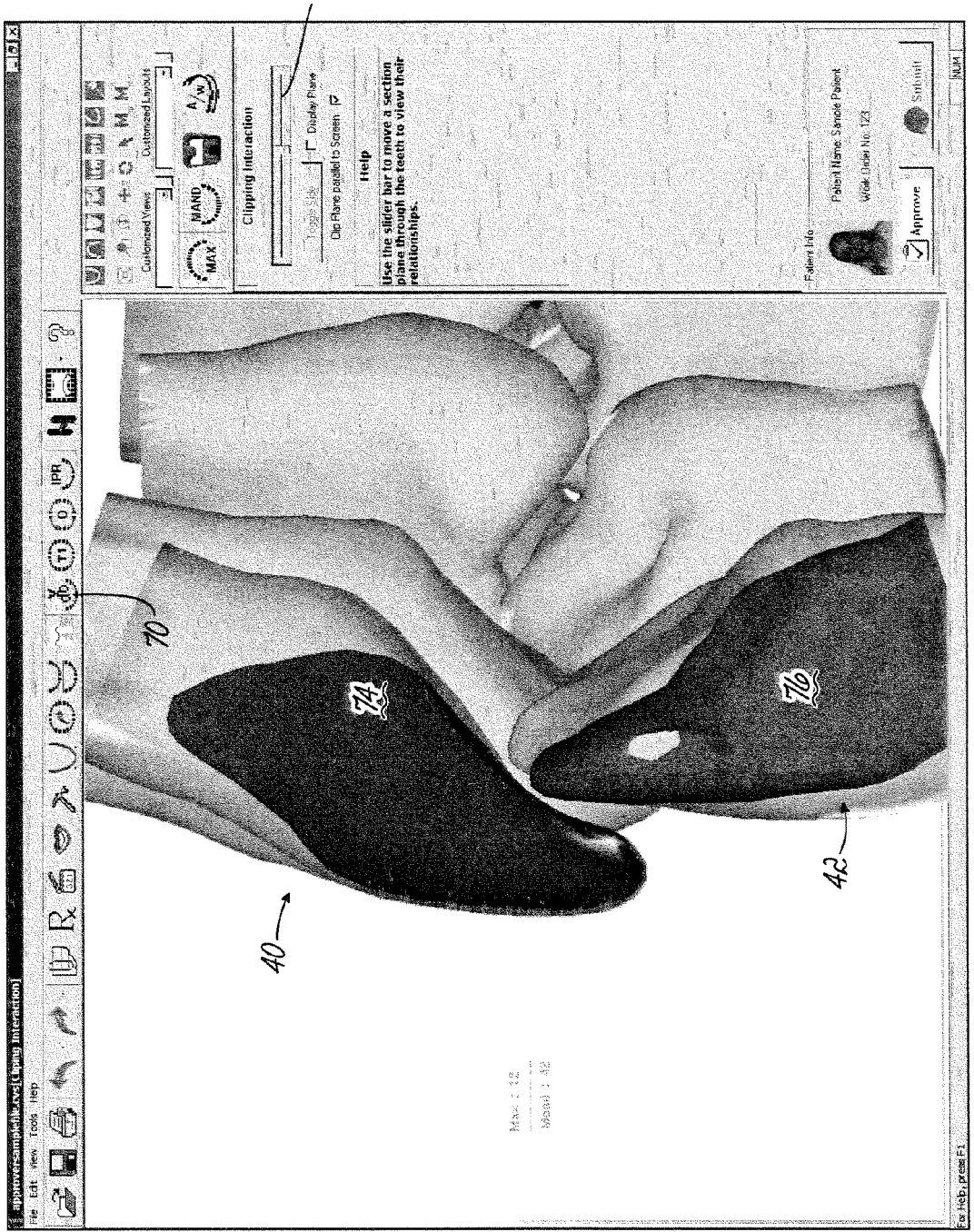
FIG. 12 contains another representative screen shot from the software showing the use of a clipping plane where the plane remains stationary and the teeth move through the plane.
Figure 13:
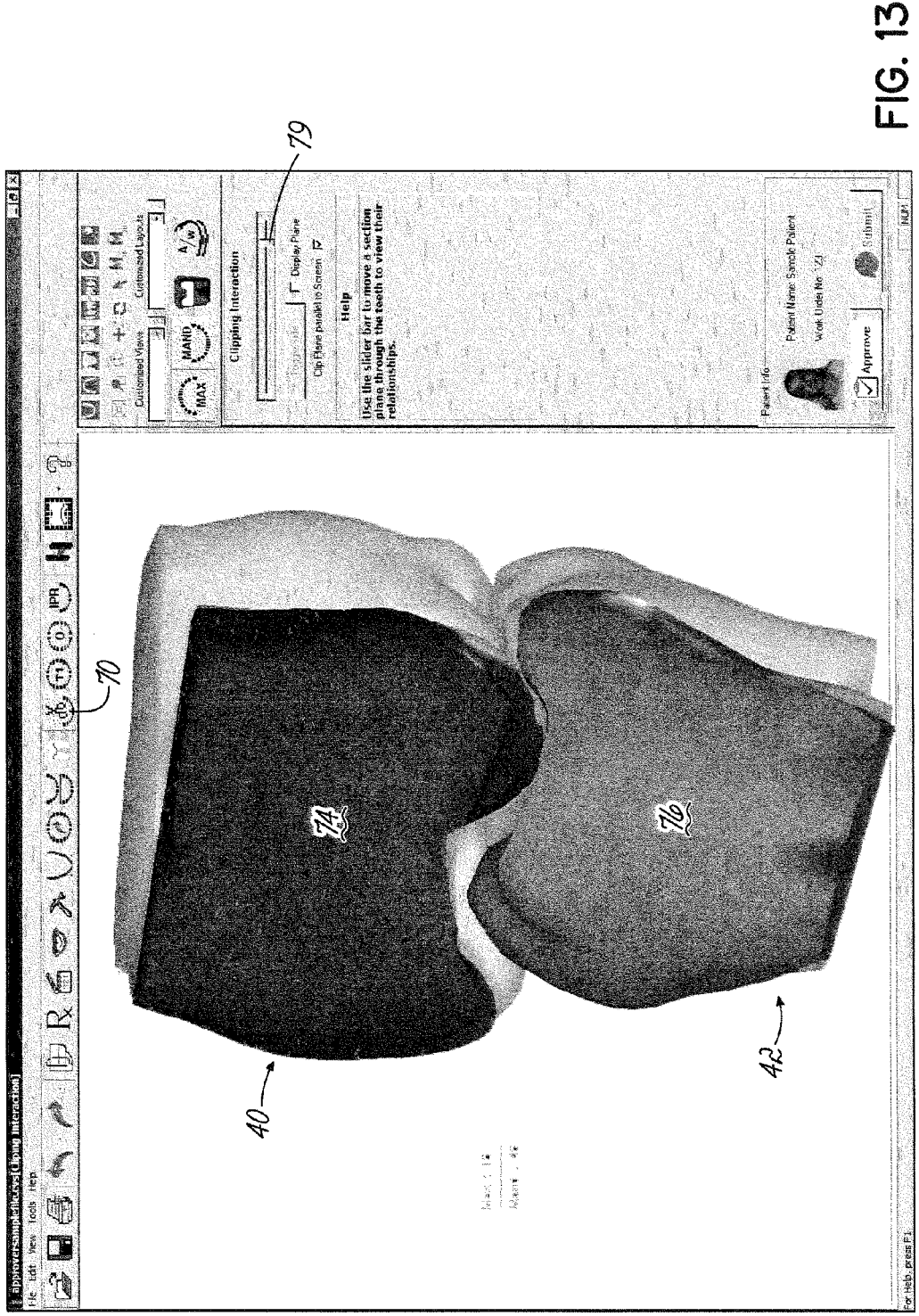
FIG. 13 contains another representative screen shot from the software showing the use of a clipping plane where the plane remains stationary and the teeth move through the plane.
Figure 14:
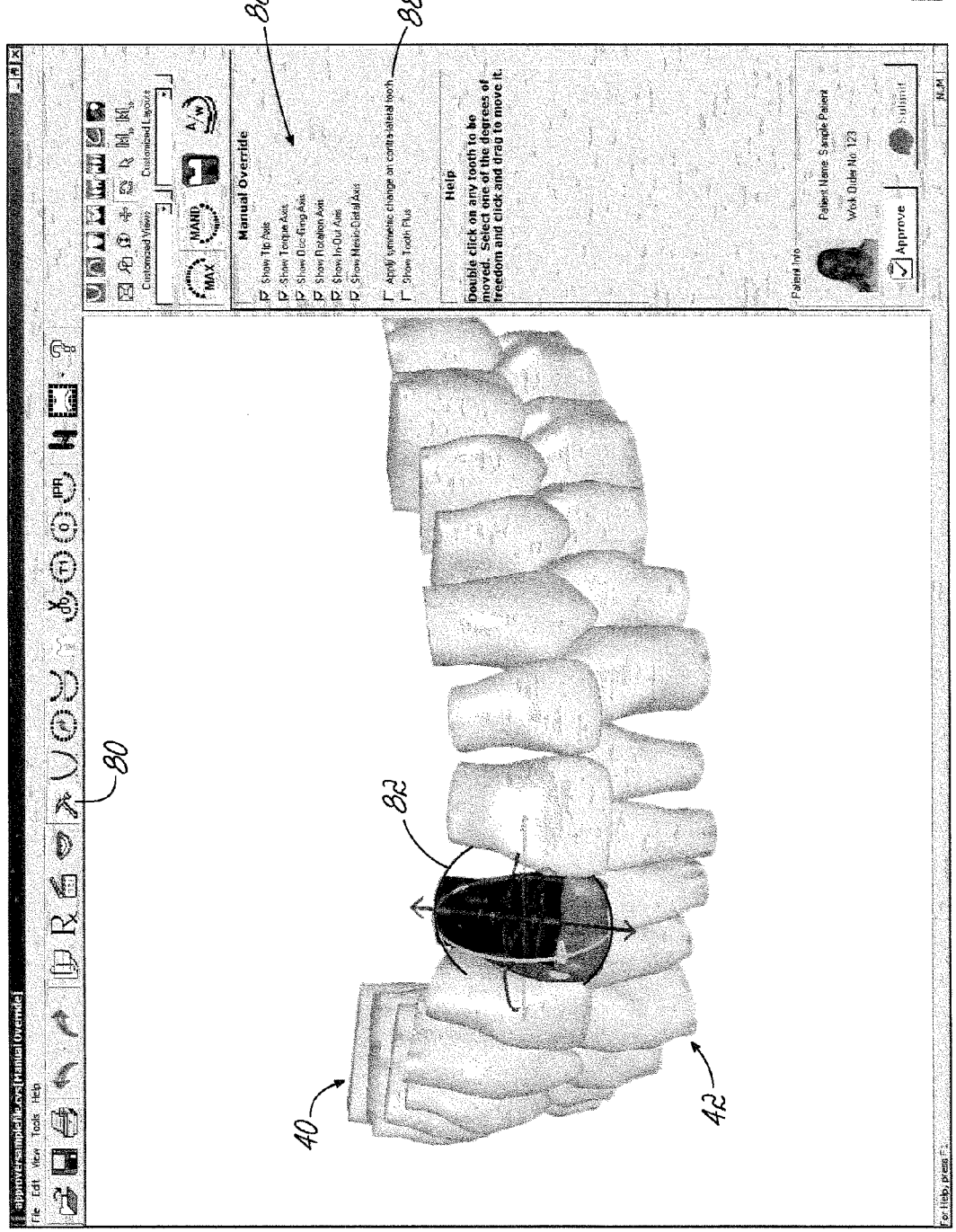
FIG. 14 contains a representative screen shot from the software showing the manual override of a position of a tooth.
Figure 15:
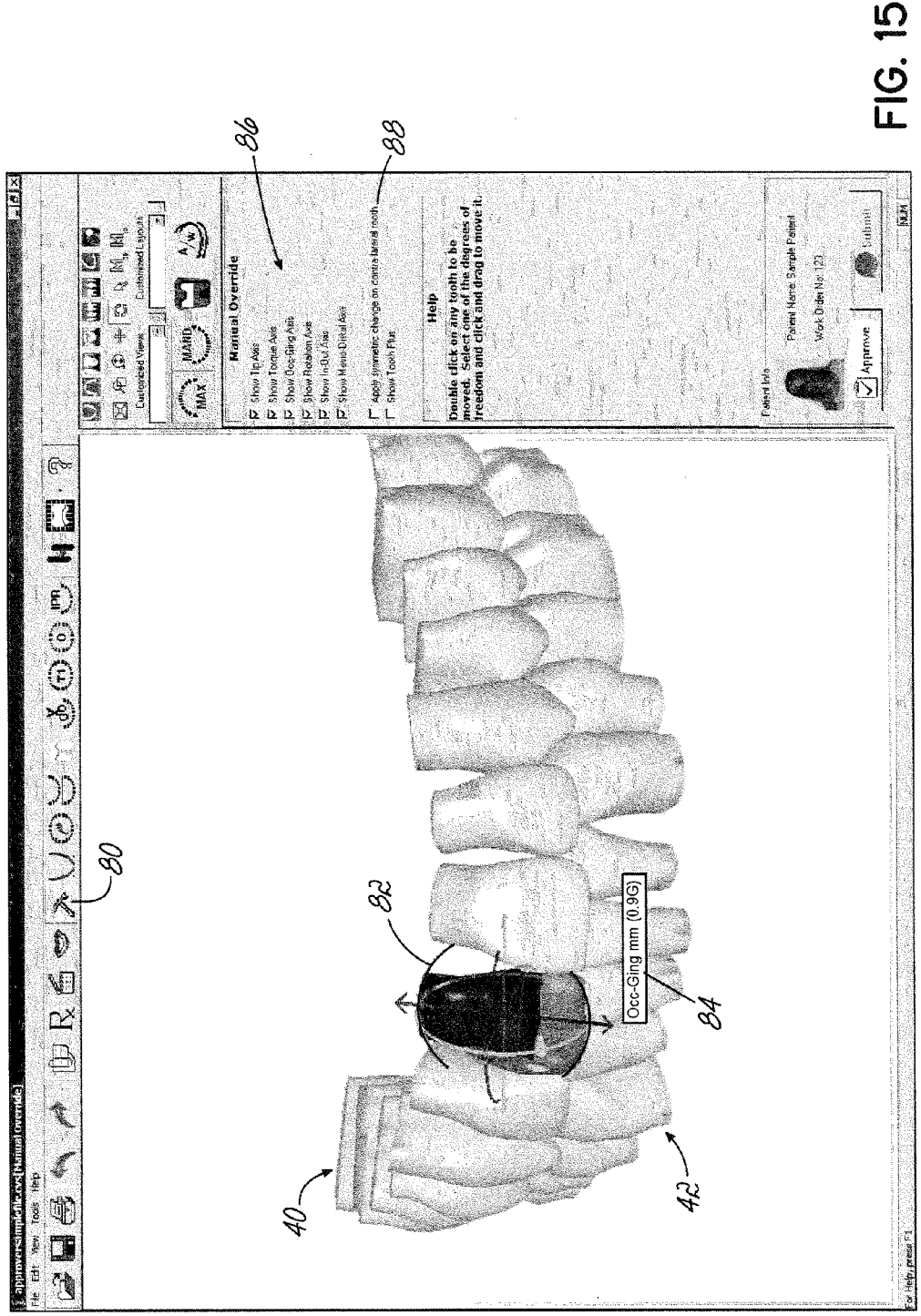
FIG. 15 contains a representative screen shot from the software showing the tooth being adjusted up and down.

Referring now to FIGS. 7 and 8, the clipping plane functionality provides a sectioned view of a tooth. A plane (clipping plane 72) is used to section the tooth. The user may toggle between:

Method 1: The clipping plane 72 will be parallel to the screen & as the user moves the plane 72 by using slider bar/dragging the mouse, the assembly 40, 42 will rotate keeping the plane parallel to the screen.

Method 2: View that was currently active, where the clipping plane 72 moves relative to the assembly 40, 42.

Clicking the "Toggle Side" Button 78 will alternate showing the assembly 40, 42 on either side of the clipping plane 72.

The clipping plane 72 may provide the user with an interactive cross sectioning of the teeth. The clipping plane operates 72 in two modes as shown above. In the first mode the teeth 40, 42 stay stationary and the clipping plane 72 moves normal to the mantrough curve. In the second mode, the clipping plane 72 is positioned parallel to the screen and remains stationary as the teeth 40, 42 are rotated through the plane. To utilize the clipping plane 72, the user selects the Clipping Interaction icon 70 from the tool bar or selects from the menu, View and Clipping Interaction. The user has the option to display a representation of the clipping plane 72 in either mode. If the user has selected to view the plane 72, a transparent, outline representation of the plane 72 is dynamically displayed on the screen as the plane 72 is moved through the teeth 40, 42. A slide bar 79 is used to move the clipping plane 72 along the mantrough curve. The cut planes 74, 76 of the teeth 40, 42 are displayed in a color other than that used for the teeth 40, 42 or the root portions to allow the user to easily identify the cut section.

In the first mode the teeth 40, 42 can be oriented in any position before or during the clipping plane 72 interaction. If the position of the teeth 40, 42 obstructs the view of the cross section 74, 76, the user may select the Toggle Side button 78, which may alternate the side of the clipping plane 72 on which the teeth 40,42 are displayed, thus eliminating the obstruction.

Referring now to FIGS. 9 through 13, the alternate mode of operation for the clipping plane 72 is to make the clipping plane 72 parallel to the screen and then move the teeth 40, 42 though the plane. An advantage of this mode of operation of the clipping plane 72 is that the clipping plane 72 is never obstructed. The parallel orientation of the clipping plane may also be useful for users in determining bite conditions and tooth overlap after the teeth 40, 42 have been adjusted. As with the first mode of operation, the user may turn on or make visible a representation of the clipping plane 72.

Referring now to FIGS. 14 through 23, by selecting Manual Override 80, a user may double click on, or otherwise select, any tooth to get a graphical display of six degrees of freedom 82 to make adjustments. Selecting one of the degrees of freedom 82 and dragging it changes the tooth orientation. When the user moves the mouse over the degrees of freedom 82, a tool-tip 84 will be shown accordingly. Double clicking on any tooth from anywhere in the software package will automatically take user to manual over-ride functionality.

The manual override function allows for a user to individually manipulate the teeth 40,42. To activate the manual override function, a user may select the Manual Override icon 80 from the tool bar, or from the menu system, select Edit and then Manual Override. The user may also simply double click on a tooth to enter the Manual Override mode from any view for that particular tooth. When a tooth has been selected for the Manual Override, a graphical representation of the six degrees of freedom 82 of movement for the tooth is displayed. The three translational degrees of freedom, Occlusal-Gingival 102, In-Out 104, and Mesio-Distal 106 move the tooth along straight lines. The three rotational degrees of freedom, Rotation 103, Tip 105, and Torque 107 rotate the tooth around the translational axes. Movement of the tooth in any of these directions is accomplished by selecting the appropriate degree of freedom with the mouse, then while holding down the left mouse button, manipulating the tooth. An advantage of having this functionality available at any time by double clicking on a tooth helps to streamline the process for fire user and may eliminate additional steps of having to leave a particular function to get to the Manual Override function to then have to return to the previous function.

The graphical representation of the six degrees of freedom 82 may be manipulated by the check boxes 86 on the manual override menu. Only those degrees of freedom checked will be displayed as can be seen in the representation of the degrees of freedom 82' in FIG. 17. The manual override may be applied to two teeth simultaneously by selecting the "Apply Symmetric Change" 88 feature on the menu. When selected any manipulations to a tooth will automatically be applied to a corresponding tooth resulting in symmetric movements of the two teeth.

Referring specifically now to FIGS. 18 through 23, when the Manual Override functionality is activated, a graphical representation of the six degrees of freedom 82 of the tooth movement is displayed on the chosen tooth. Each of these degrees of freedom is represented by a graphical arrow 102-107, which may be selected by the user. When a degree of freedom is selected with the mouse, a Tool-tip 84 containing the description of that degree of freedom and a numerical value of the relative movement for that degree of freedom is displayed. Holding down the left mouse key allows the user to drag the arrow in the direction of the mouse movement. This in turn moves the tooth. As the arrow and the tooth are being moved, the numerical value of the relative movement for the degree of freedom is being updated in real time. Predetermined limits bound the movements for each of the degrees of freedom. When the limit for the movement is reached, the movement stops and the user is warned that the operation would exceed the maximum allowed limit. The six degrees of freedom that can be adjusted, as mentioned above and seen in the FIGS. 18 through 23, are the three translational degrees of freedom, Occlusal-Gingival 102, In-Out 104, and Mesio-Distal 106, and the three rotational degrees of freedom. Rotation 103, Tip 105, and Torque 107.

Figure 24:
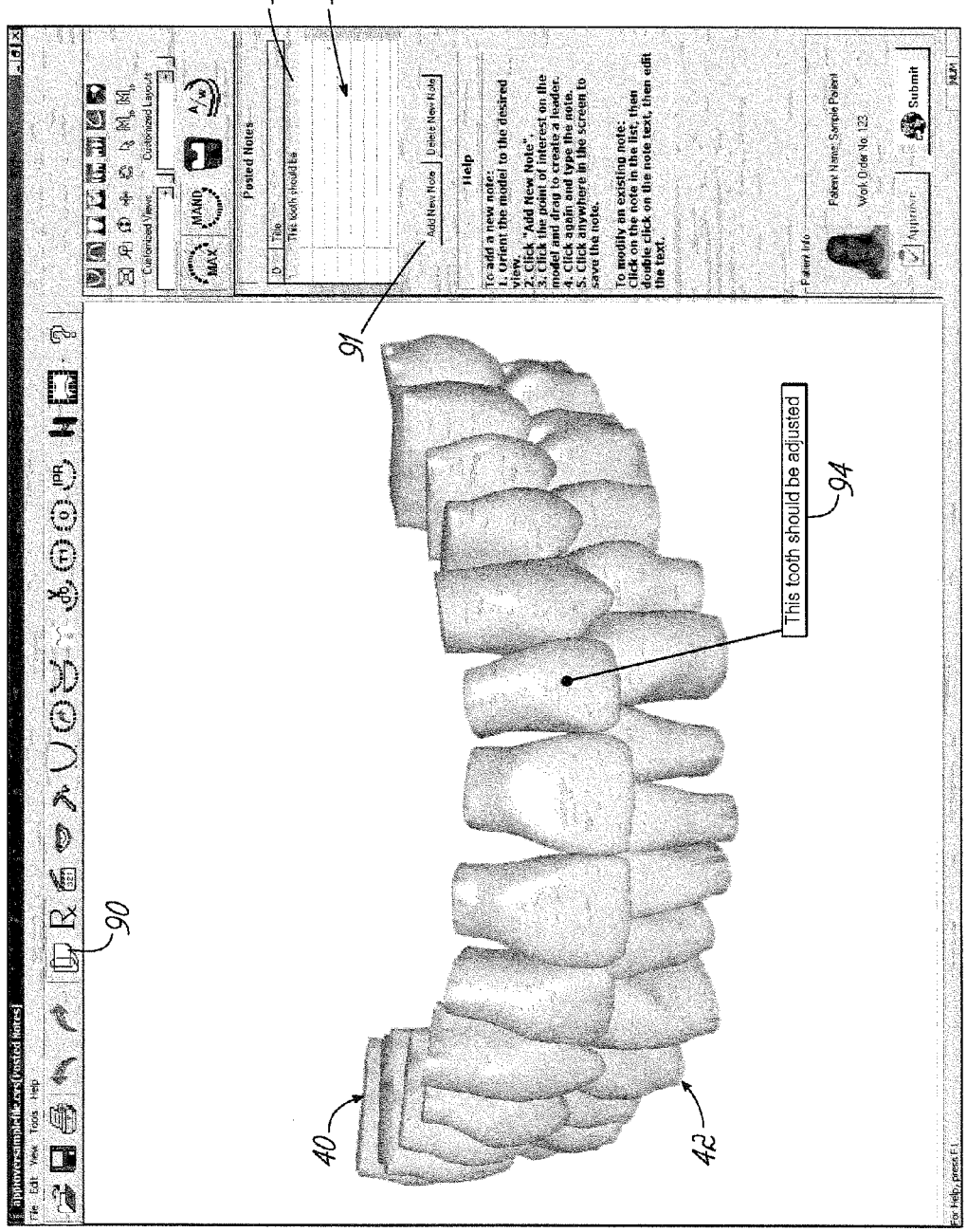
FIG. 24 contains a representative screen shot from the software showing a tooth being marked with an associated note.
Figure 25:
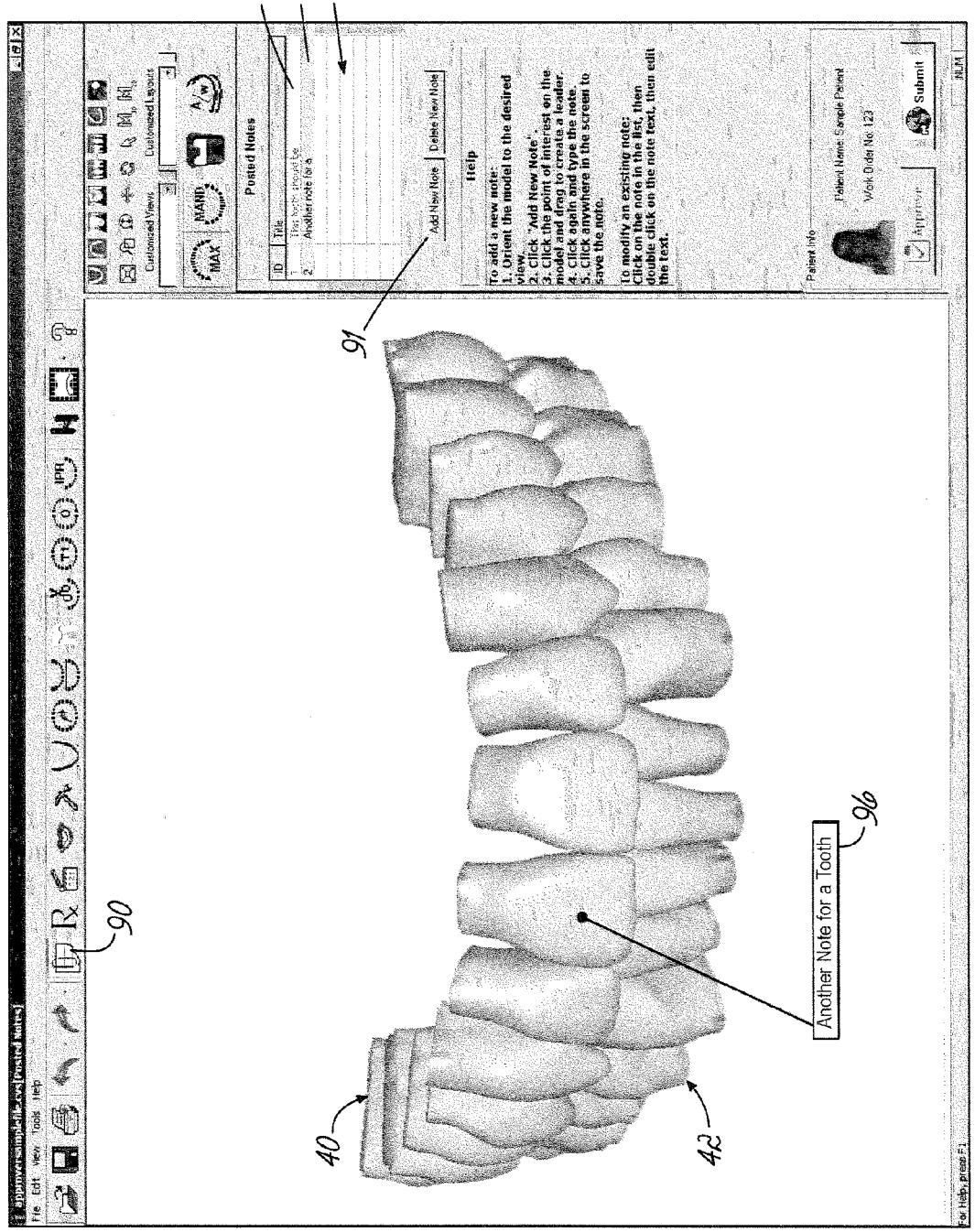
FIG. 25 contains a representative screen shot from the software showing an alternate tooth being marked with an associated note.
Figure 26:
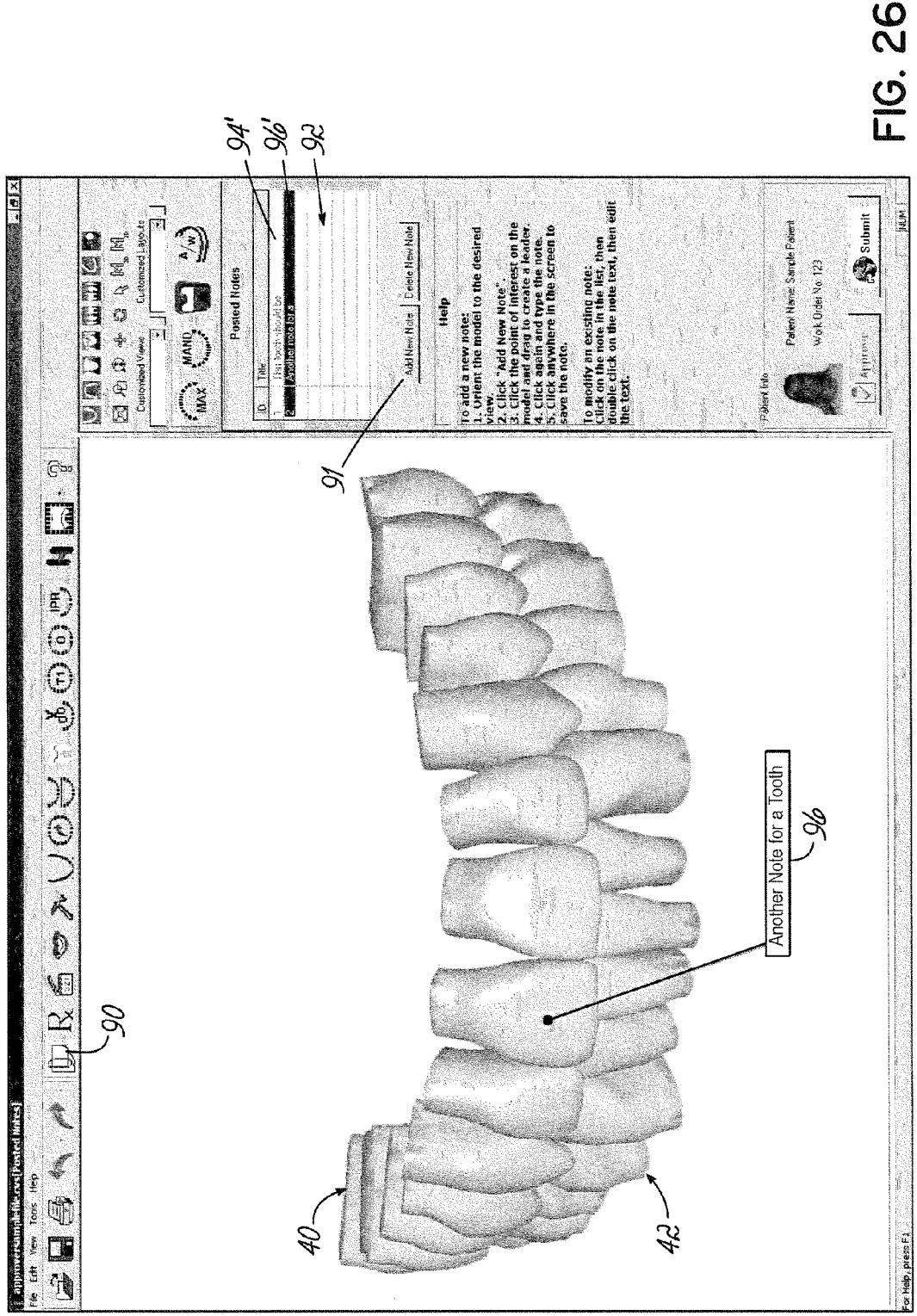
FIG. 26 contains a representative screen shot from the software showing the corresponding note on the tooth when the note is selected form the menu on the right.

Referring now to FIGS. 24 through 26, the user may add graphically linked notes to individual teeth. To add or view notes, the user may select the Posted Notes icon 90 from the tool bar or from the menus, Edit and then Posted Notes, Once at the Posted Notes menu, the user may Add New Note 91, which will prompt the user for a note caption, a summary, in which the user may include any type of textual information that he/she would like to be associated with the tooth. To add a note 94, 96, the user selects an anchor location on a tooth and drags a lead line off the tooth to create a text box 94', 96'. The user may then type text in the text box 94', 96'. After the note has been entered in the text box 94', 96', the text will be added to the list of notes 92. Once a number of notes have been entered, the user may either select the note based on its caption 94', 96' from the list of notes available.

Figure 27:
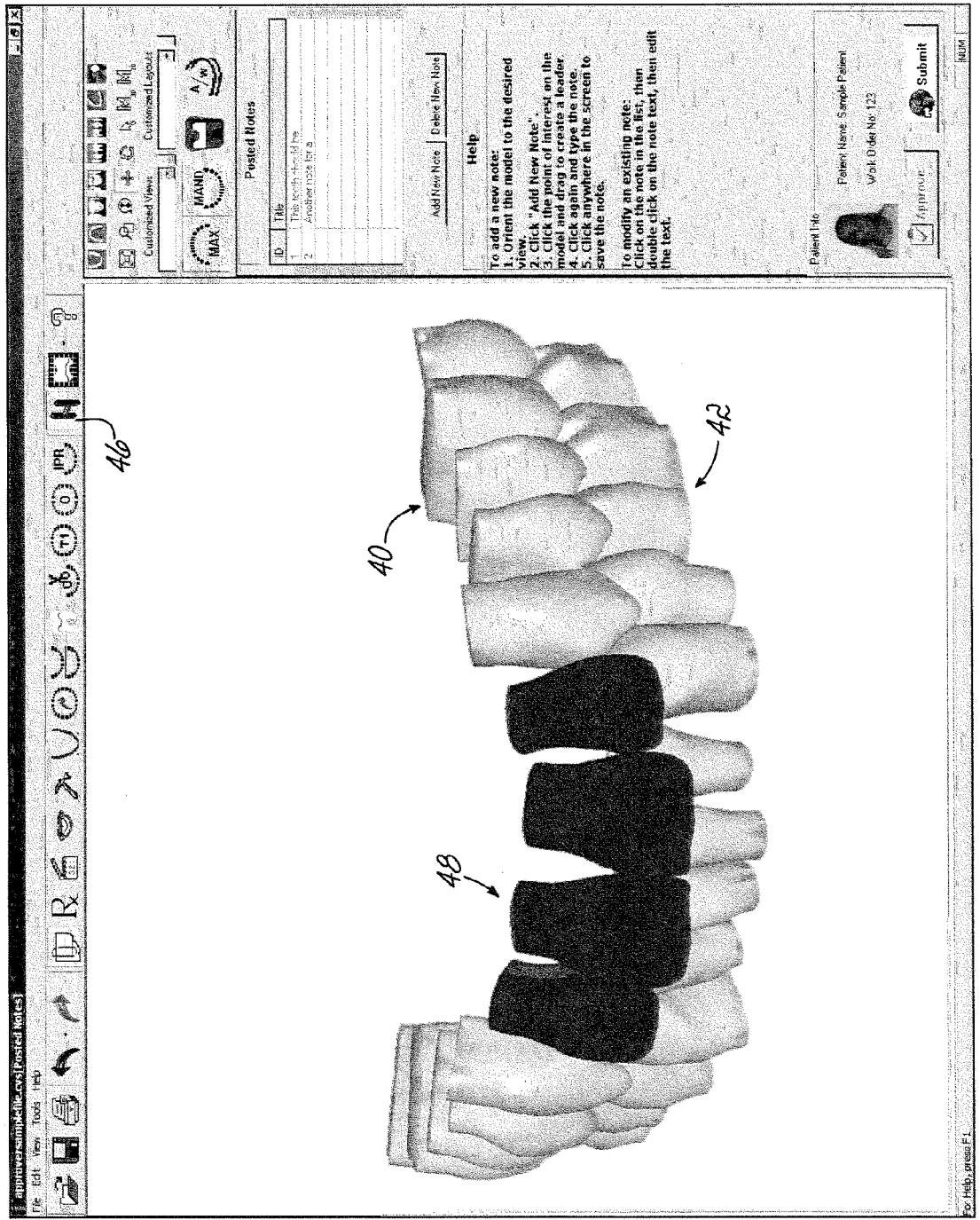
FIG. 27 contains a representative screen shot from the software showing the highlighting of teeth that have been moved from their original position.
Figure 28:
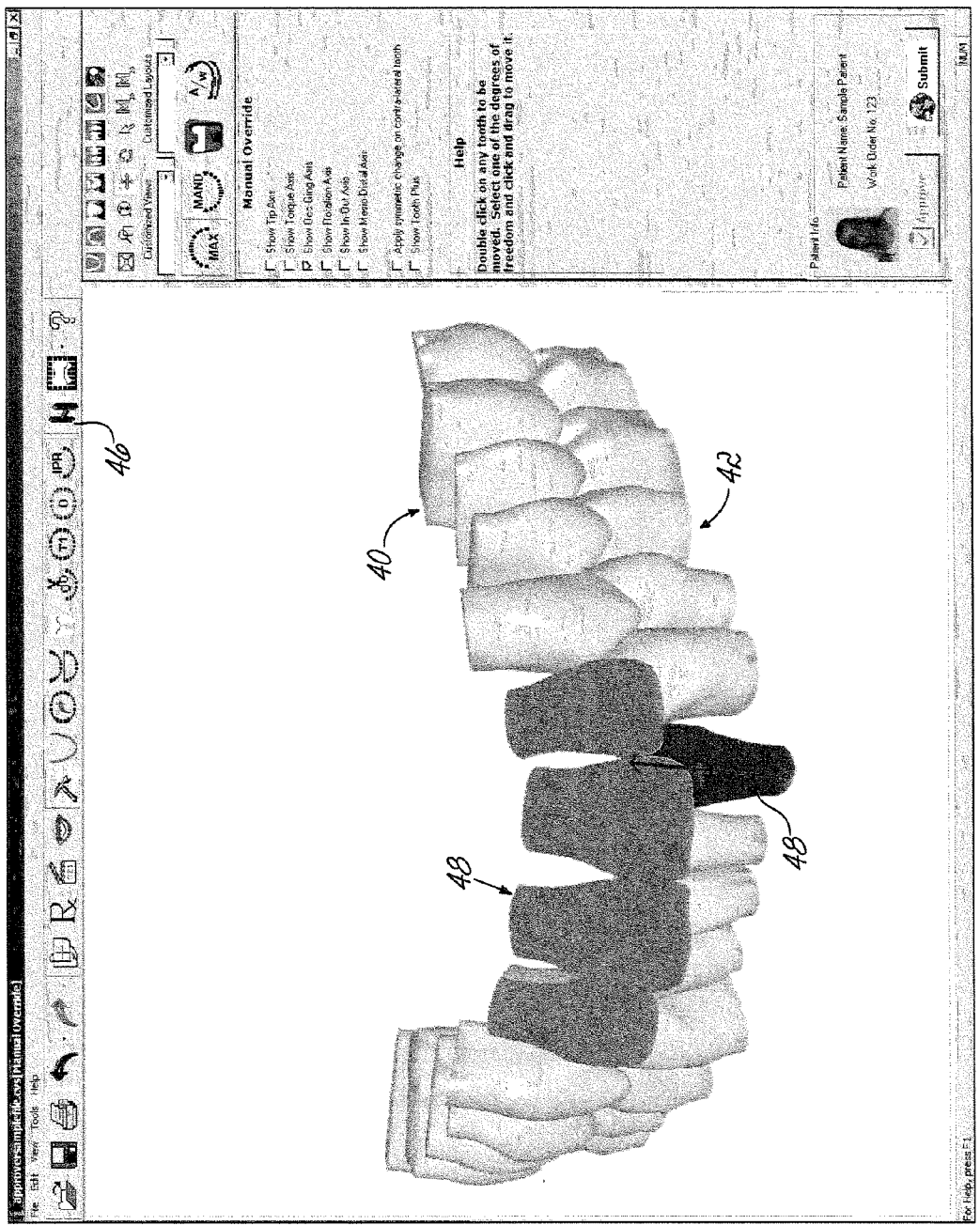
FIG. 28 contains another representative screen shot from the software showing the highlighting of teeth that have been moved from their original position.

Referring now to FIGS. 27 and 28, the "H" Button 46 in the main toolbar will toggle the color of teeth 40, 42 based on whether they have changed position relative to their original setup. Movements of teeth when viewed in one orientation may not be readily apparent to users when the teeth are being displayed in an alternate orientation. This can be particularly true if the movements to the teeth are very slight. To assist users in determining which teeth have been adjusted, the H tool will highlight 48 any tooth that has been moved since the last saved position. To enable the highlighting function, the user may select the Toggle Changed Tooth Highlighting icon 46 from the tool bar or from the menus select View and then Toggle Changed Tooth Highlighting. Selecting this option the first time will toggle the feature to be on. When the highlighting feature is on, any tooth that is not in its original position from the last saved configuration is colored differently 48 from the other teeth 40, 42 that have not moved. Once the teeth that have been moved have been identified, the user may disable the tooth highlighting by again selecting the Toggle Changes Tooth Highlighting icon 46 from the tool bar or from the menus selecting View and then Toggle Changed Tooth Highlighting which toggles the highlighting feature to be off. The color of a tooth will automatically change any time a tooth is moved when the highlighting feature is toggled on. There is no need to toggle the highlighting between on and off to update the colors on the teeth that have moved.

Figure 29:
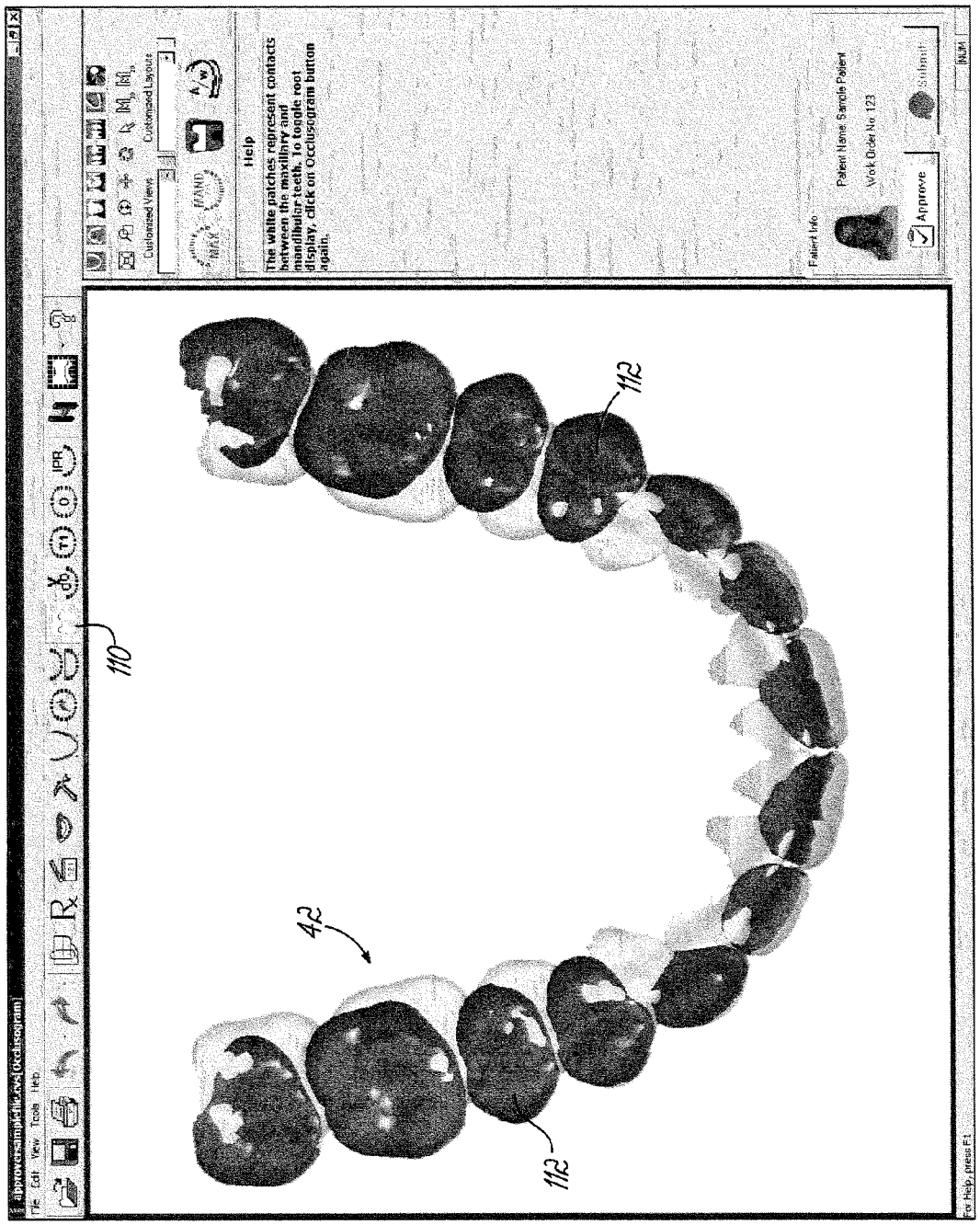
FIG. 29 contains a representative screen shot from the software showing the simulation of occlusal points.

Referring now to FIG. 29, the Occlusogram tool is used as a pictorial representation of the amount of interference 112 between the tooth mass of the mandibular 42 and maxillary 40 assemblies. The tool can be accessed by selecting the Occlusogram icon 110 from the tool bar or from the menu system by selecting View and then Occlusogram. The pictorial representation shows different levels of intersection between the teeth. This tool may be used to replace or augment the current manual practice of using carbon paper to check tooth alignment. This tool, used in conjunction with the clipping plane tool may be helpful to the user of the software in determining and correcting tooth alignment when teeth incorrectly overlap or intersect, ultimately affecting the bite.

Figure 30:
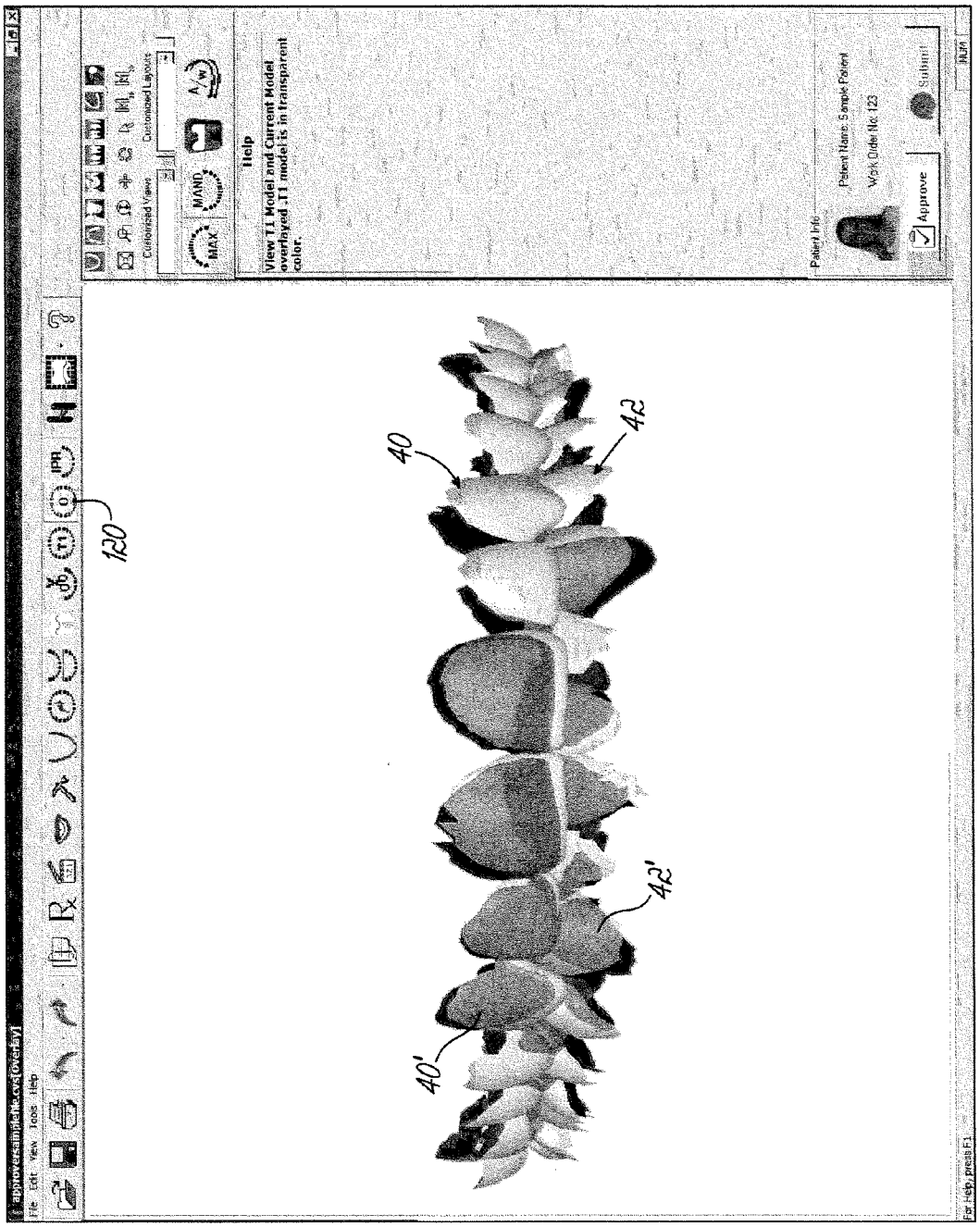
FIG. 30 contains a representative screen shot from the software showing the maloccluded model overlaying the current model.

Referring not to FIG. 30, the overlay function may be selected using the overlay icon 120 or from the menus by selecting View and then overlay assemblies. This option may be used to show the original assemblies 40', 42' and assemblies after treatment 40, 42 overlaying each other for visual comparison.

Figure 31:
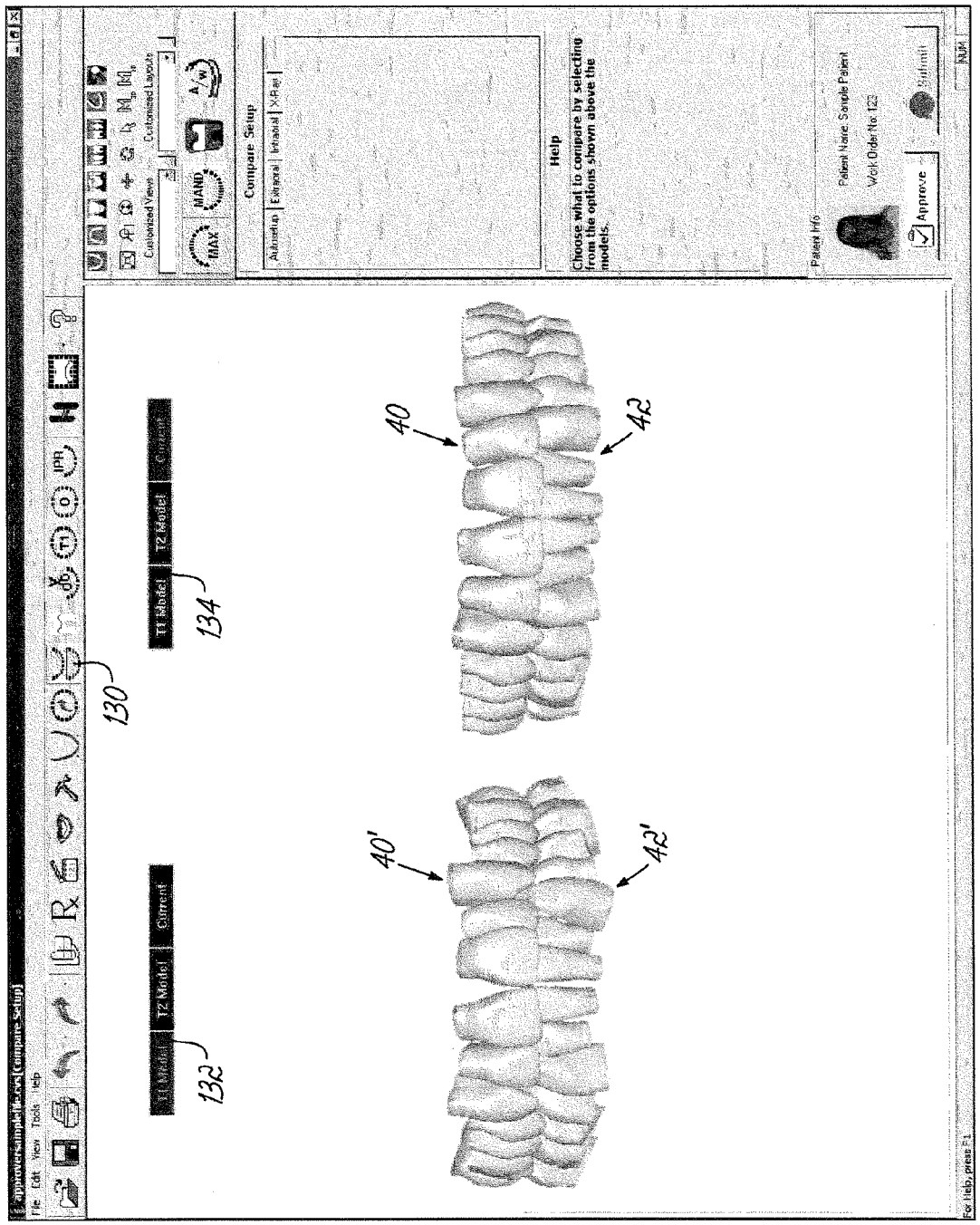
FIG. 31 contains a representative screen shot from the software showing the ability to compare models side by side.
Figure 32:
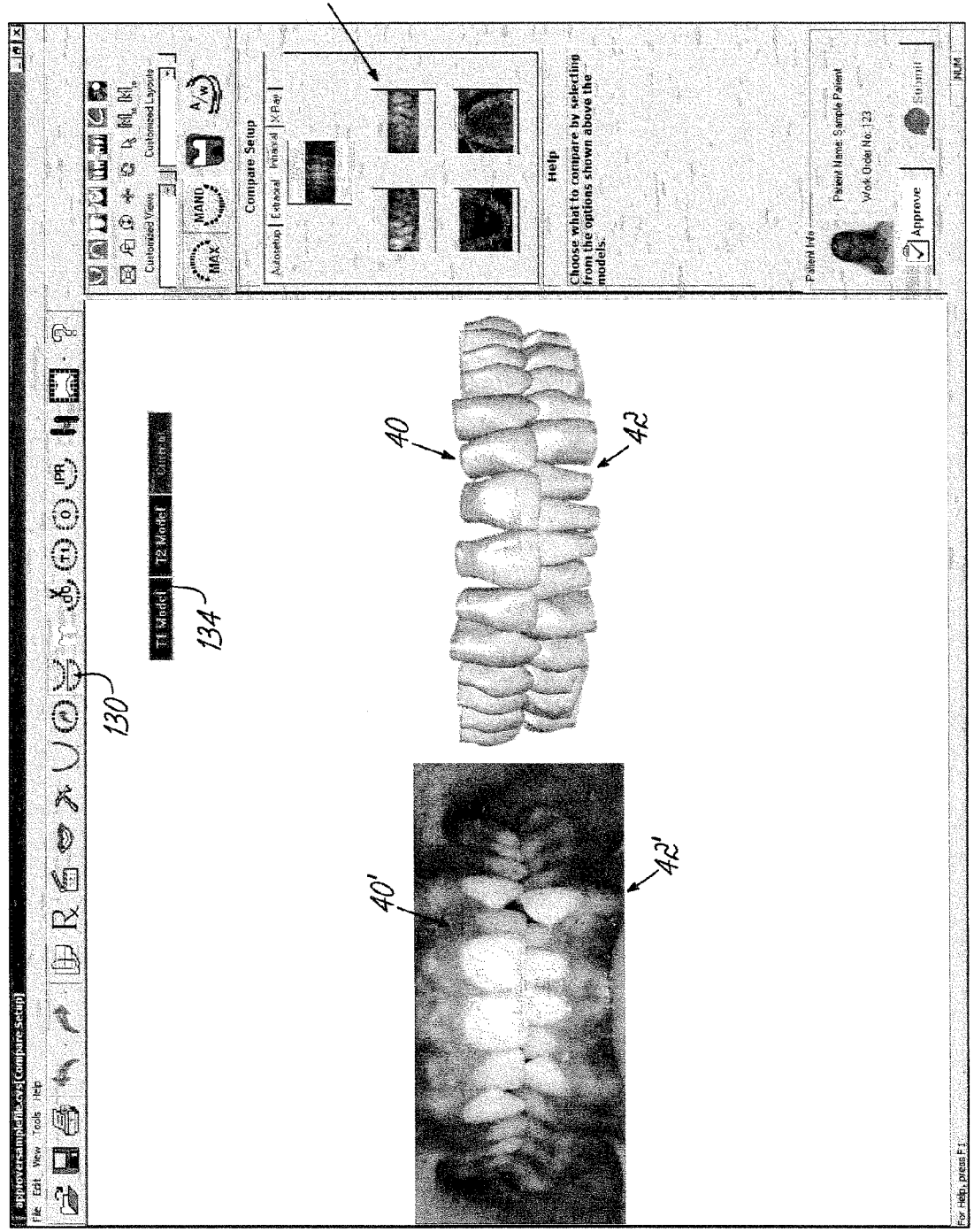
FIG. 32 contains a representative screen shot from the software showing a comparison between a patient's actual teeth and a computer model.

Another method for comparing may be seen in FIGS. 31 and 32. The side by side comparison may be activated when a user selects the Compare Setup icon 130. The view area is divided in half and the user may then select what is to be shown in each half. Model data may be selected from the view menus 132, 134. Alternatively one of the views may show real patient pictures for comparison by making a selection form the menu 136 as best seen in FIG. 32.

Figure 33:
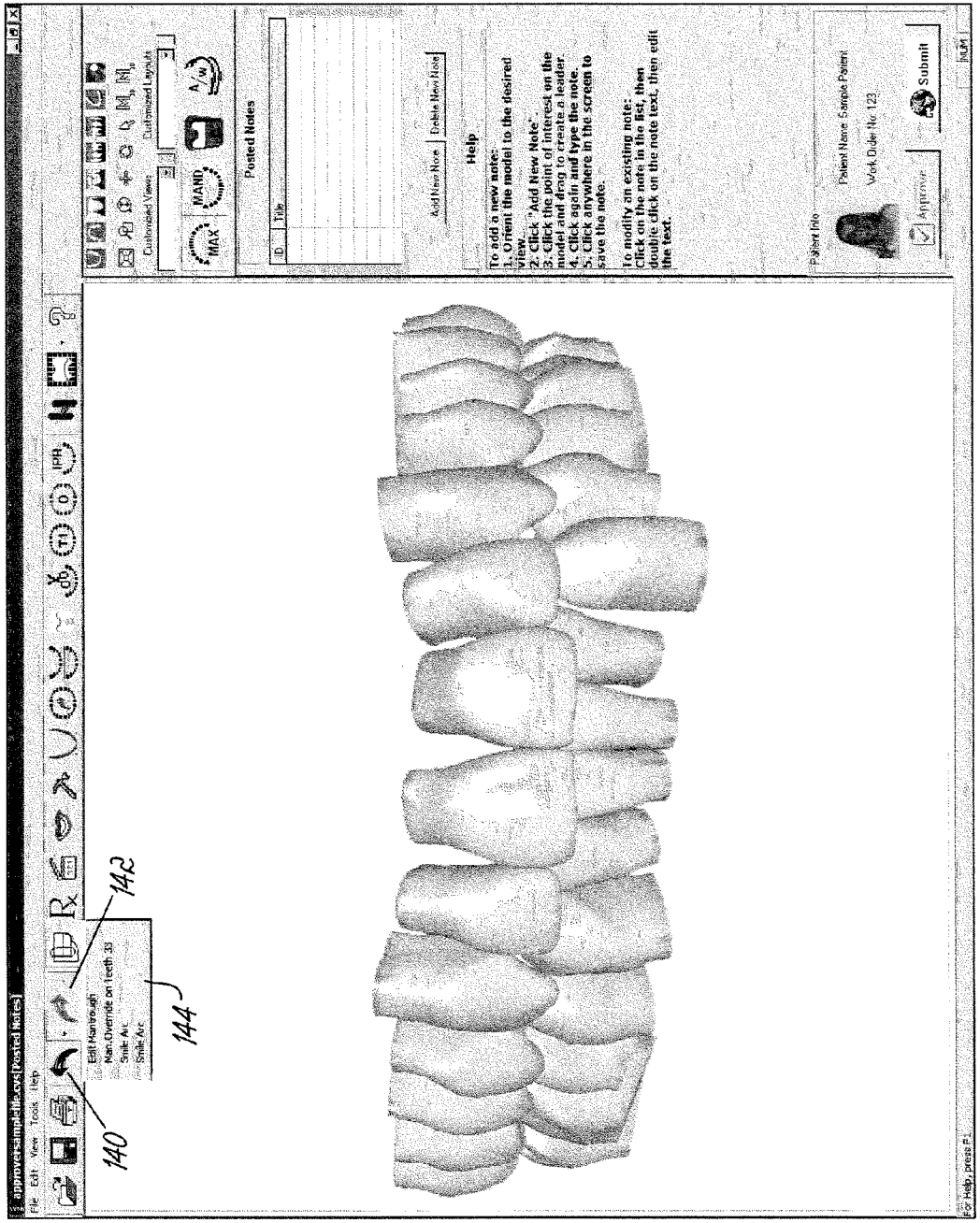
FIG. 33 contains a representative screen shot from the software showing the multilevel undo function.

Referring now to FIG. 33, after the user performs any editing operation, undo 140 and redo 142 buttons become active. Using the drop down menu 144 the user can undo/redo multiple edits with one mouse pick.

The user has access to a sequential undo function. The software is capable of undoing all actions in the reverse order of their creation up to the last point at which the configuration was saved. The user may access the Undo function through the menus by choosing Edit and then Undo. The user may also access the Undo function by selecting the Undo icon 140 on the tool bar. An advantage for the user in using the icon on the tool bar is that the icon 140 also has a pull down menu 144 that allows the user to access a list of all of the users actions since the last save. If the user selects one of the actions in the middle of the list, the software will undo all of the actions up to and including that action. This functionality assists a user in undoing a group of actions that may have lead to an unsatisfactory result.

In conjunction with the sequential Undo, the user also has access to a sequential redo function that works like the undo function in reverse. The Redo function may also be accessed through the menu system by selecting Edit and then Redo. The user may also access the Redo icon 142 on the tool bar. Like the Undo icon 140, the Redo icon 142 may also contain a pull down menu (not shown) listing all of the commands that were executed. If the user uses the pull down menu 144 to undo a plurality of commands from the undo pull down menu 144 and then realizes that he/she went too far by mistake, the user may use the Redo icon 142 and pull down menu to reconstruct the commands that were inadvertently undone. The ability to undo and redo commands coupled with the ability to pick from a list of executed commands and have the software either undo back to that point or redo up to that point provides power and flexibility to the user when manipulating objects on the display.

Figure 34:
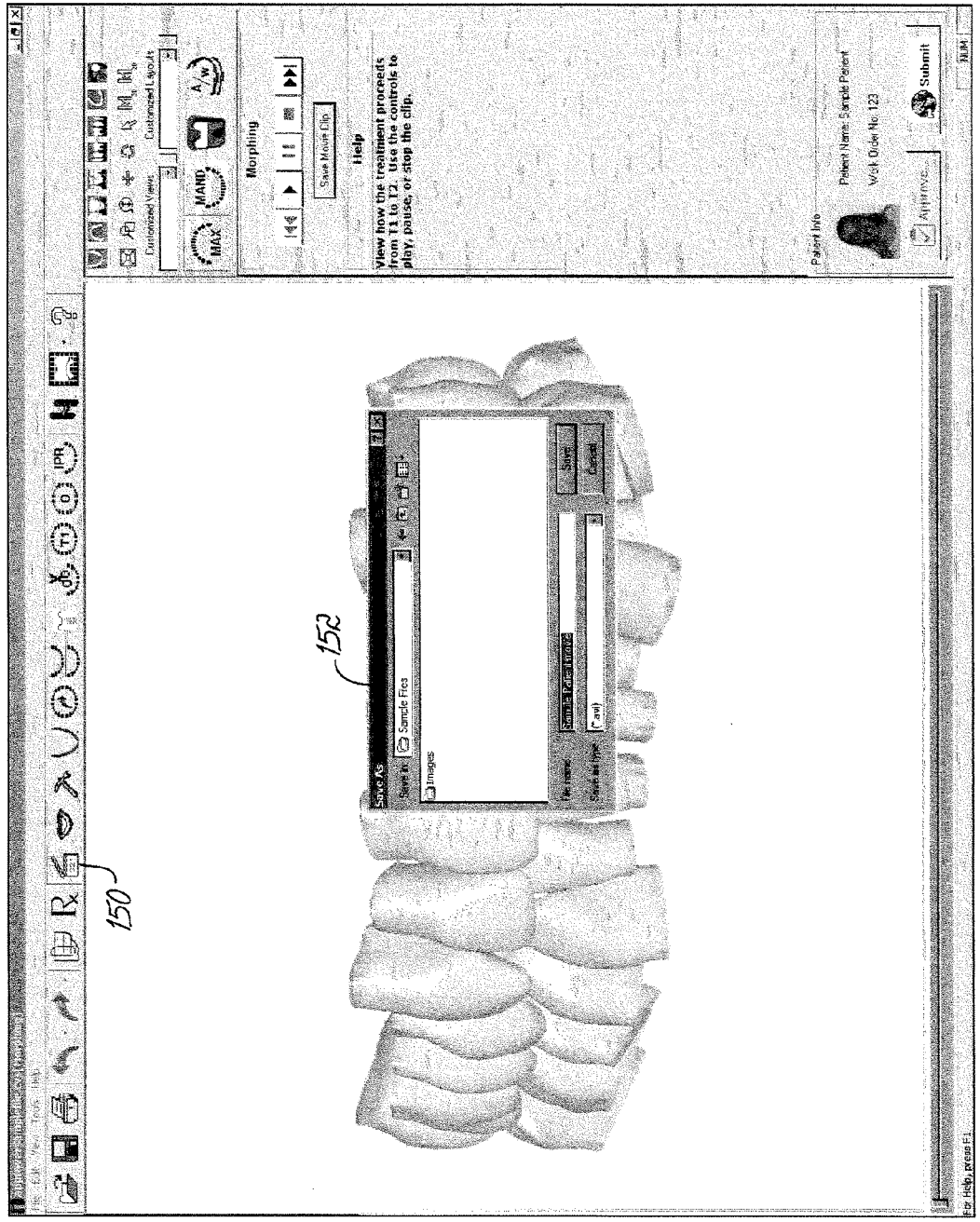
FIG. 34 contains a representative screen shot from the software showing the ability to save animation sequences.

Referring now to FIG. 34, the user may create with button 150 animation sequences of the teeth 40, 42 moving from an original position to a new adjusted position so that the patients may see the effects with dialog 152 of the adjusted teeth. As an added benefit, the user may save this animation sequence in a computer compatible movie file that the user may then send home with the patient. This feature may be used as a marketing tool for an office that uses the software program as that it could be viewed as an added service provided by the office for its patients.

Figure 35:
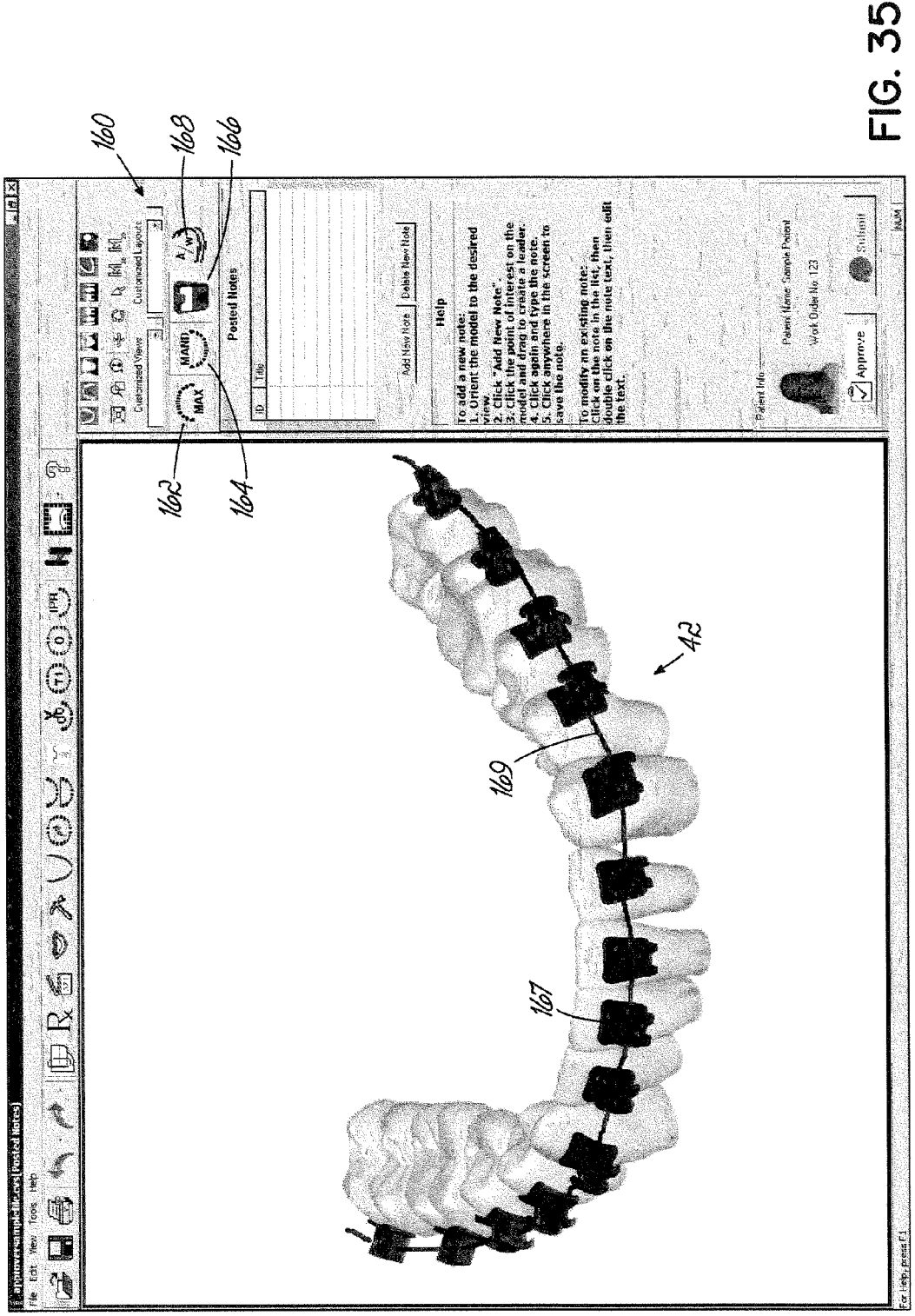
FIG. 35 contains a representative screen shot from the software showing the teeth in the mandible containing brackets and an archwire.

The software may be configured with a viewing toolbar 160, which assists a user in quickly changing from one orientation or view to another. The maxillary teeth 40 may be displayed or removed by toggling the maxillary icon 162. Similarly the mandibular teeth 42 may be displayed or removed by toggling the mandibular icon 164. An icon 166 for the brackets 167 may be toggled to display the brackets 167 on the teeth 42 as best seen in FIG. 35. Likewise an icon 168 for the arch wire 169 may be toggled to display the archwire on the teeth 42 as also seen in FIG. 35.

Figure 36A:
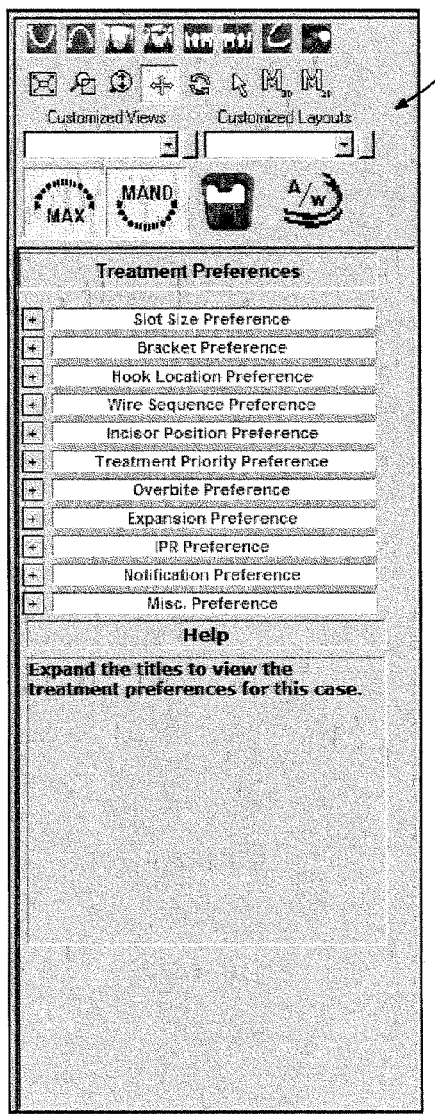
FIG. 36A contains a representative screen shot of a portion of the software showing a menu for treatment preferences.
Figure 36B:
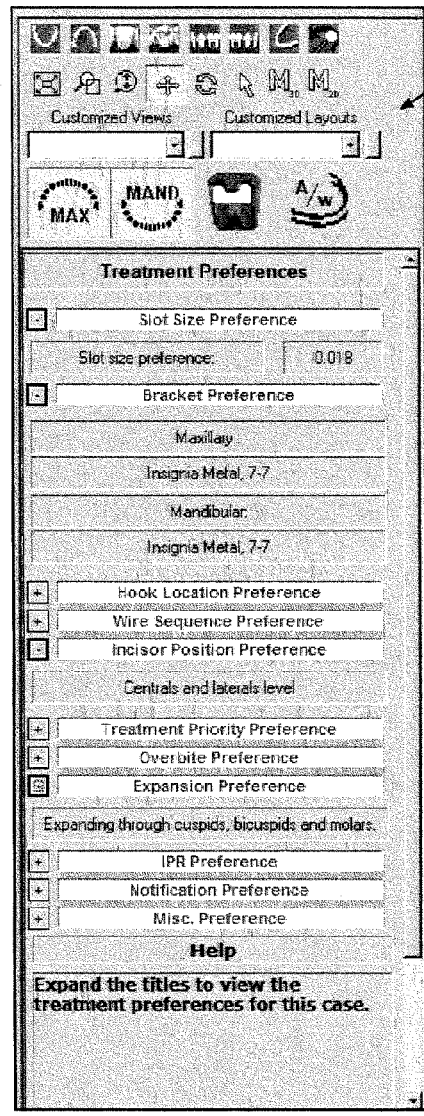
FIG. 36B contains a representative screen shot of the portion of the software shown in FIG. 36A with some treatment preference menus expanded.

Preferences for the treatment of a patient associated with the brackets and archwires, as well as any other applicable appliance may be set up in the menus for treatment preferences 170 as seen in FIGS. 36A and 36B. The menu has expandable categories 170', which may be adjusted prior to delivery of the software package or in other embodiments, directly be the user. These preferences will then be the preferences for designing for a particular case and in some embodiments may not be overwritten by a Doctor's default preferences.

While the present invention has been illustrated by a description of various embodiments and while these embodiments have been described in considerable detail, it is not the intention of the applicants to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the spirit or scope of applicants' general inventive concept.

On the other hand, the descriptions and illustrations of the various embodiments themselves include novel and inventive details, features and sub-combinations thereof, which applicant reserves the right to claim in the prosecution of this international and subsequent national applications or in divisional or other applications related thereto.

What is claimed is:

1. A computer-implemented method to identify an orthodontic treatment plan applicable to teeth of a human patient, the method comprising:
    displaying a three-dimensional perspective representation of the teeth of the patient to a user;
    receiving from the user a selection of one or more teeth of the orthodontic treatment plan and displaying a three-dimensional perspective representation of six degrees of freedom of movement of the selected one or more teeth, each degree of freedom presented by a graphical direction of adjustment of the one or more teeth consistent with the three-dimensional perspective representation of the teeth;

receiving from the user an adjustment of the selected one or more teeth of the orthodontic treatment plan along a direction of movement selected from the six degrees of freedom; and moving at least one tooth of the teeth of the patient to a new position on the display corresponding to the adjustment.

2. The computer-implemented method of claim 1 wherein receiving an adjustment from the user includes the user selecting a first degree of freedom from the six degrees of freedom of movement through user input, and the moving includes moving the selected tooth in the direction of the first degree of freedom in response to user input causing movement of a pointing device on the selected tooth.

3. The computer-implemented method of claim 2 wherein receiving an adjustment from the user includes selecting a second degree of freedom from the six degrees of freedom of movement through user input, and the moving includes moving the selected tooth in the direction of the second degree of freedom in response to user input causing movement of a pointing device on the selected tooth.

4. The computer-implemented method of claim 2 further comprising:
limiting movement of the position of the tooth in the direction of the degree of freedom by predetermined bounds.

5. The computer-implemented method of claim 2 further comprising:
recording the movement of the selected tooth as it is performed by a user;
maintaining a sequential list of the recorded movement and additional recorded movements; and
allowing the user to back up to a previous recorded movement in the sequential list of recorded movements,
wherein a current movement of the selected tooth is undone.

6. The computer-implemented method of claim 5 further comprising:
allowing the user to move forward though the sequential list of recorded movements to a recorded movement,
wherein an undone movement of the selected tooth is performed again.

7. The computer-implemented method of claim 5 further comprising:
providing the user with a control to select a previous recorded movement of the selected tooth anywhere in the sequential listing; and
causing all intervening recorded movements from the selected recorded movement to be undone.

8. The computer-implemented method of claim 7 further comprising:
providing the user with a control to select a previous recorded movement of the selected tooth in the sequential listing that has been undone; and
causing all intervening recorded movements from the selected recorded movement to be performed again.

9. The computer-implemented method of claim 1 wherein the orthodontic treatment plan comprises a control point on a curve, the method further comprising:
associating at least a portion of the teeth of the patient with the curve;
adjusting a shape of the curve by moving the control point in response to user input; and
moving the portion of the teeth associated with the curve to a new position based on the adjusted shape of the curve.

10. The computer-implemented method of claim 9 wherein the movement of the portion of the teeth associated with the curve occurs in real time with the adjustment of the shape of the curve.

11. The computer-implemented method of claim 9 wherein the movement of the control point is limited by predetermined bounds.

12. The computer-implemented method of claim 9 wherein the curve is a smile arc and associating at least a portion of the teeth of the patient with the curve comprises:
fixing a first end point of the smile arc to a first cuspid;
fixing a second end point of the smile arc to a second cuspid; and
interpolating the arc through two additional points on a first and second maxillary incisor, wherein the smile arc spans four front teeth.

13. The computer-implemented method of claim 9 wherein the curve is a mantrough curve and associating at least a portion of the teeth of the patient with the curve comprises:
overlaying an archform curve with a portion of the teeth of the patient in the mandible using mathematical methods.

14. The computer-implemented method of claim 13 further comprising:
displaying distances between corresponding teeth on opposites sides of the mandible.

15. The computer-implemented method of claim 14 further comprising:
displaying a change in distance from a first, original distance between the corresponding teeth and a second distance between the corresponding teeth after the mantrough curve has been adjusted.

16. The computer-implemented method of claim 13 further comprising:
simultaneously display an original representation of the mantrough curve in addition to the adjusted mantrough curve.

17. The computer-implemented method of claim 13 wherein moving the control point causes symmetric movement of the portion of the teeth.

18. The computer-implemented method of claim 8 further comprising:
recording the movement of the control point as it is performed by a user;
maintaining a sequential list of the recorded movement and additional recorded movements; and
allowing the user to back up to a previous recorded movement in the sequential list of recorded movements,
wherein a current movement of the control point is undone.

19. The computer-implemented method of claim 18 further comprising:
allowing the user to move forward though the sequential list of recorded movements to a recorded movement,
wherein an undone movement of the control point is performed again.

20. The computer-implemented method of claim 18 further comprising:

providing the user with a control to select a previous recorded movement of the control point anywhere in the sequential listing; and causing all intervening recorded movements from the selected recorded movement to be undone.

21. The computer-implemented method of claim 20 further comprising:

providing the user with a control to select a previous recorded movement of the control point in the sequential listing that has been undone; and causing all intervening recorded movements from the selected recorded movement to be performed again.

22. The computer-implemented method of claim 1 further comprising:

retrieving an initial position of a tooth among the representation of the teeth of the patient;

determining a position of the tooth subsequent to orthodontic treatment;

comparing the initial position of the tooth to the subsequent position of the tooth; and in response to the subsequent position being different from a current position, highlighting the tooth.

23. The method of claim 22 wherein highlighting comprises:

changing a color of the displayed representation of the tooth.

24. The method of claim 22 further comprising:

highlighting the tooth in real time as soon as it is moved from the initial position.

25. The method of claim 1 further comprising:

displaying a pictorial representation of an amount of interference between a tooth mass of a mandibular assembly and a maxillary assembly.

26. A system for identifying an orthodontic treatment plan applicable to teeth of a human patient, the system comprising:

a user interface for interfacing with a computer program;

the computer program configured to interact with a user through the user interface to display a three dimensional perspective representation of the teeth of the patient, select one or more teeth of the orthodontic treatment plan, display a three-dimensional perspective representation of six degrees of freedom of movement of the selected one or more teeth, each degree of freedom presented by a graphical direction of adjustment of the selected one or more teeth of the orthodontic treatment plan consistent with the three-dimensional perspective representation of the teeth, adjust a target for the orthodontic treatment plan, and move at least one tooth of the teeth of the patient to a new position corresponding to the adjustment.

27. The system of claim 26 wherein the target for the orthodontic treatment plan is a selected tooth, the computer program further configured to interact with the user to:

select a first degree of freedom from the six degrees of freedom of movement through user input; and move the selected tooth in the direction of the first degree of freedom in response to user input causing movement of a pointing device on the selected tooth.

28. The system of claim 26 wherein the target for the orthodontic treatment plan is a control point on a curve, the computer program further configured to interact with the user to:

associate at least a portion of the teeth of the patient with the curve;

adjust a shape of the curve by moving the control point in response to user input; and move the portion of the teeth associated with the curve to a new position based on the adjusted shape of the curve.

29. The system of claim 26 wherein after interaction with the user, the computer program is further configured to:

retrieve an initial position of a tooth among the representation of the teeth of the patient;

determine a position of the tooth subsequent to orthodontic treatment;

compare the initial position of the tooth to the subsequent position of the tooth; and in response to the subsequent position being different from a current position, highlight the tooth.

* * * * *

UNITED STATES PATENT AND TRADEMARK OFFICE
CERTIFICATE OF CORRECTION

| | | |
|---|---|---|
| PATENT NO. | : 9,529,970 B2 | Page 1 of 2 |
| APPLICATION NO. | : 12/280915 | |
| DATED | : December 27, 2016 | |
| INVENTOR(S) | : Craig A. Andreiko | |

It is certified that error appears in the above-identified patent and that said Letters Patent is hereby corrected as shown below:

In the Specification

Column 1, Line 46, delete "... ideal positions, lire most common, ...", insert --... ideal positions. The most common, ...--.

Column 1, Line 53, delete "One arch wire is provided for the upper teeth and one for tire ...", insert --One arch wire is provided for the upper teeth and one for the ...--.

Column 2, Line 49, delete "This modification may lake the form ...", insert --This modification may take the form ...--.

Column 3, Line 9, delete "If they are placed to close to the ...", insert --If they are placed too close to the ...--.

Column 4, Line 48, delete "... manipulating the tooth positions by allowing to orthodontist ...", insert --... manipulating the tooth positions by allowing the orthodontist ...--.

Column 5, Line 4, delete "... to the orthodontist, which teeth have ...", insert --... to the orthodontist which teeth have ...--.

Figure 16:
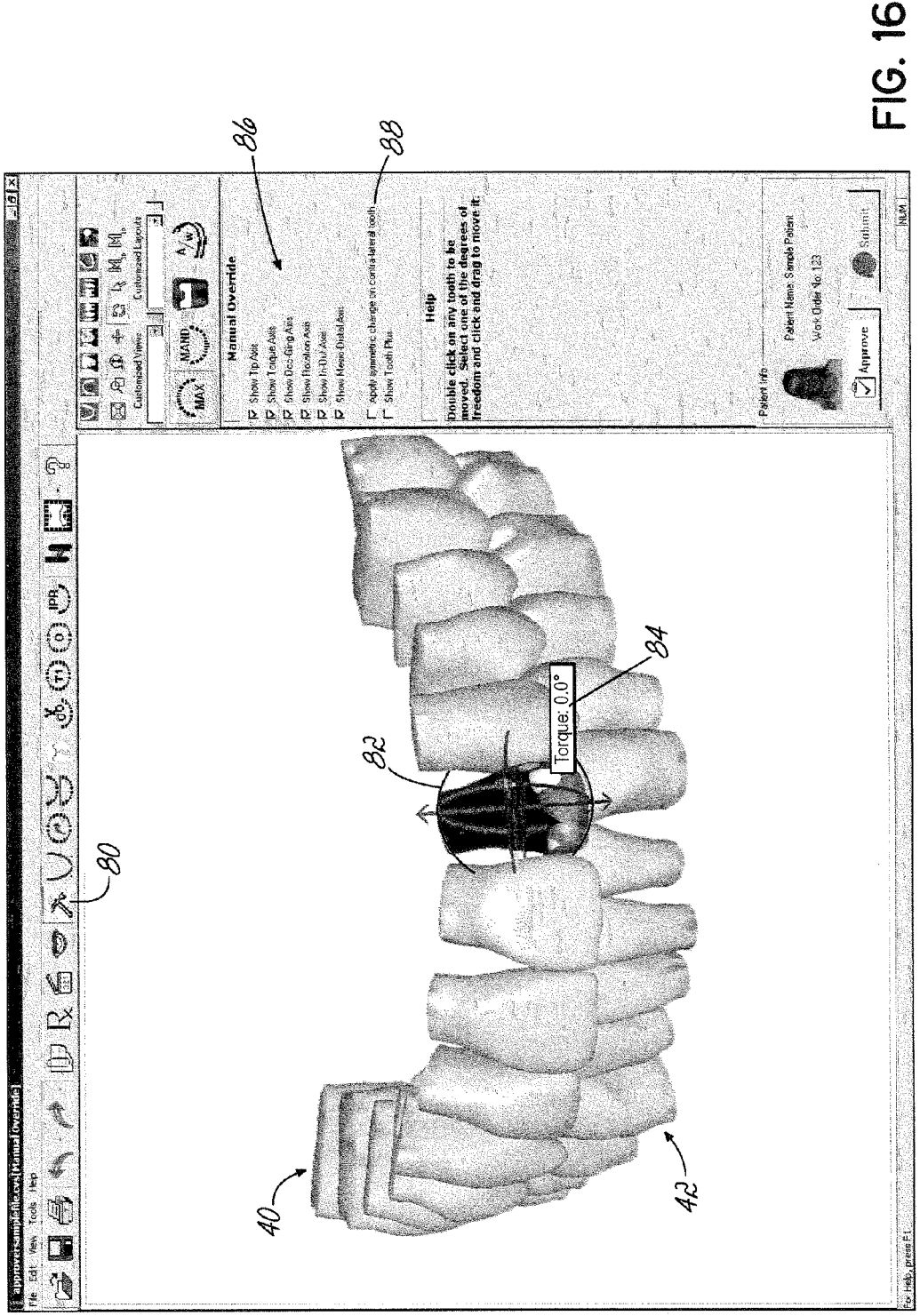
FIG. 16 contains a representative screen shot front the software showing the tooth being adjusted by twisting front to back.
Figure 17:
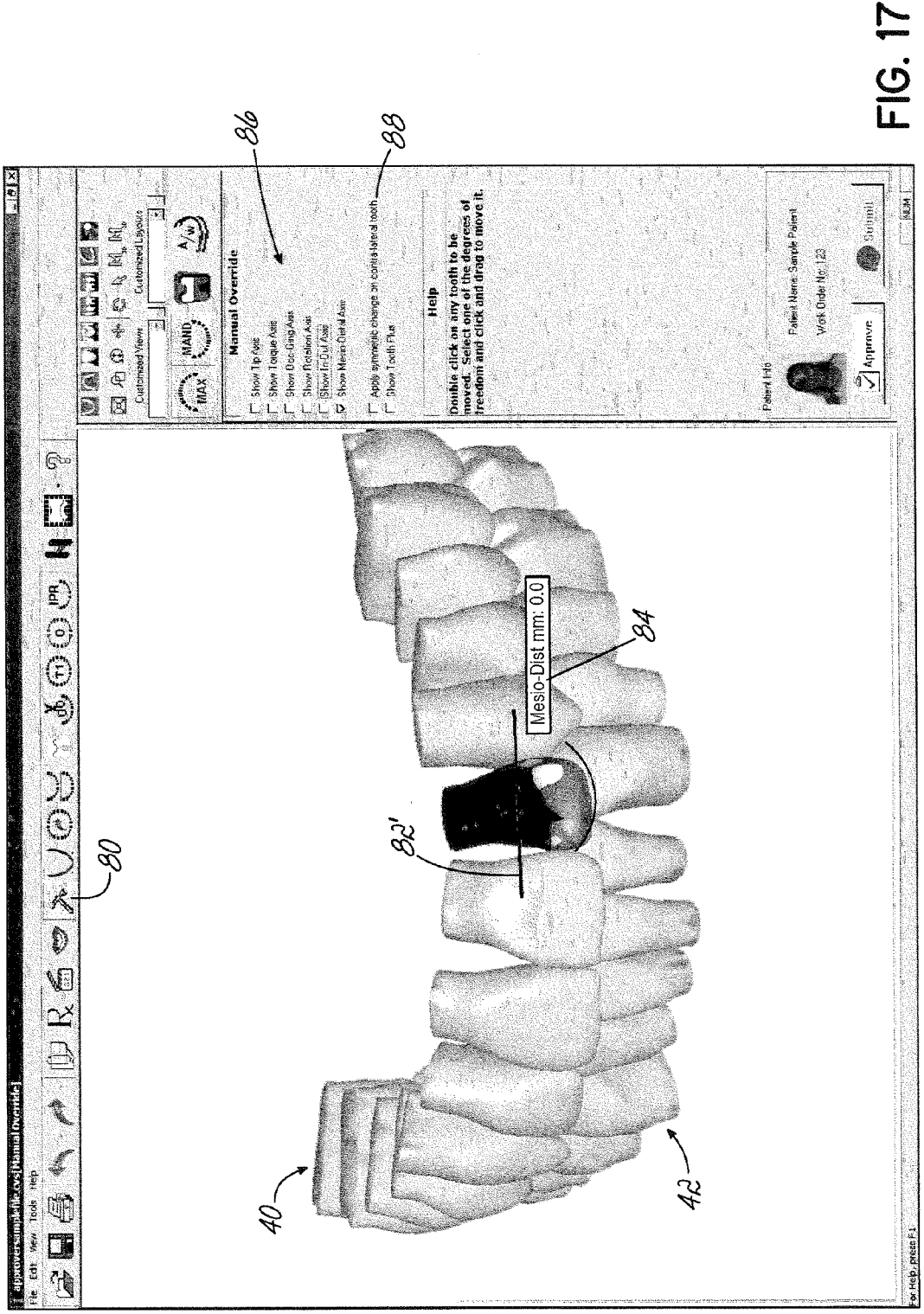
FIG. 17 contains a representative screen shot from the software showing the tooth being adjusted by moving left to right.
Figure 19:
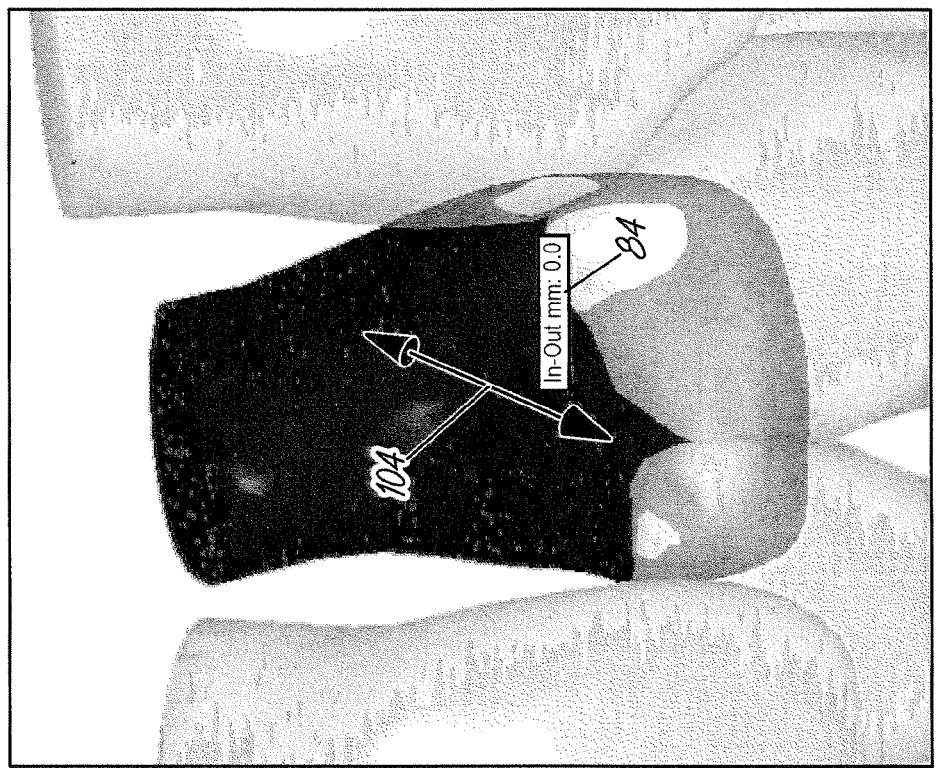
FIG. 19 contains a close up screen shot from the software showing the In-Out translational degree of freedom of movement.
Figure 18:
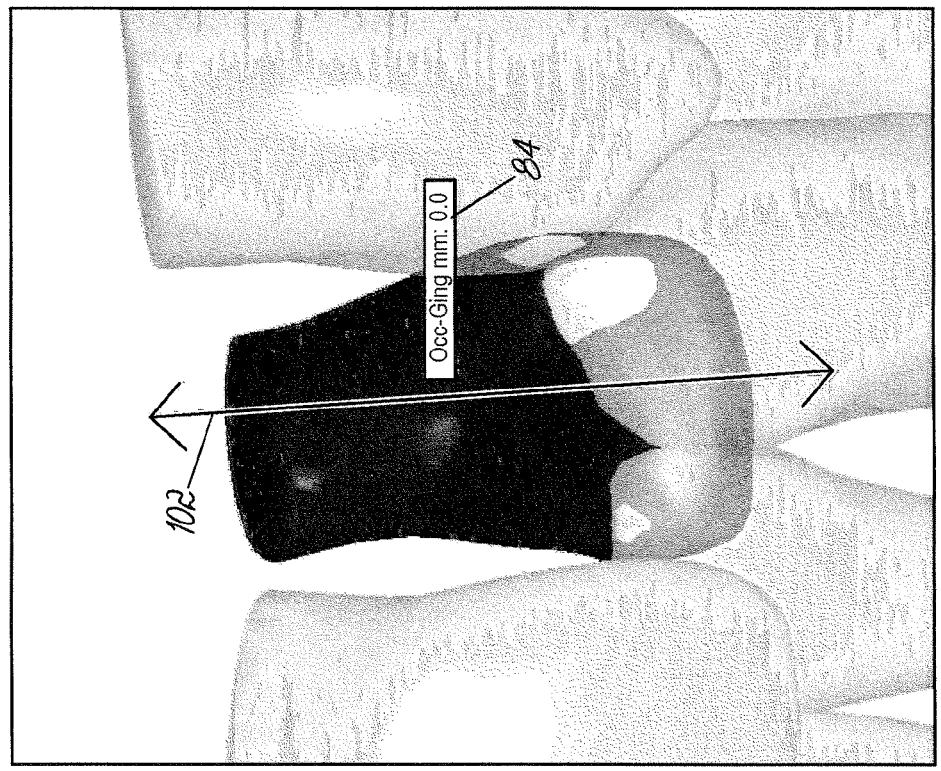
FIG. 18 contains a close up screen shot from the software showing the Occlusal-Gingival translational degree of freedom of movement.
Figure 21:
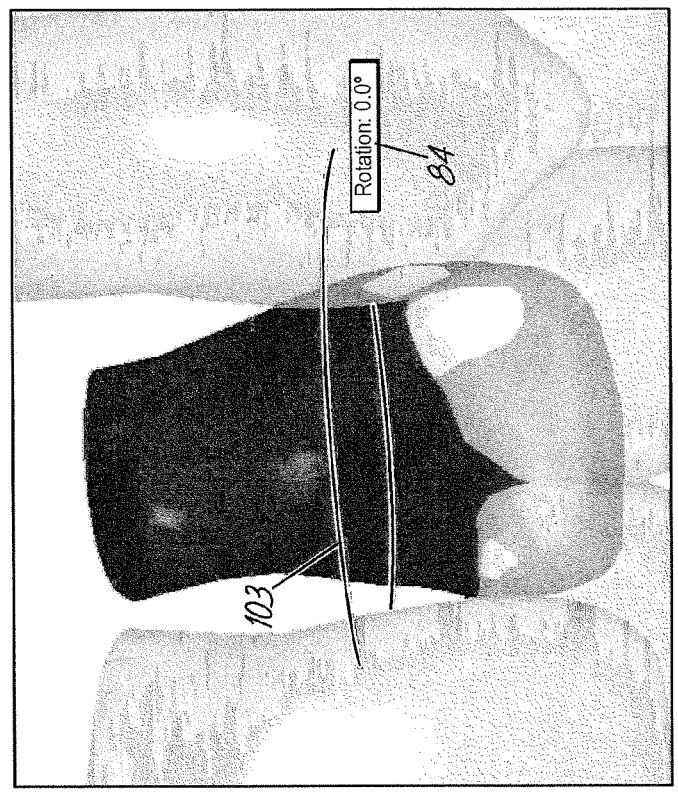
FIG. 21 contains a close up screen shot from the software showing the Rotation rotational degree of freedom of movement.
Figure 20:
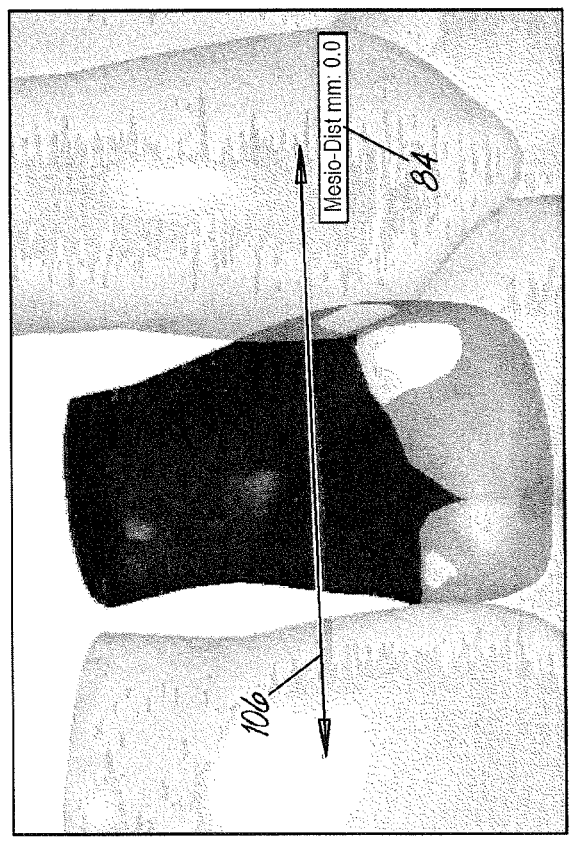
FIG. 20 contains a close up screen shot from the software showing the translational Mesio-Distal degree of freedom of movement.
Figure 23:
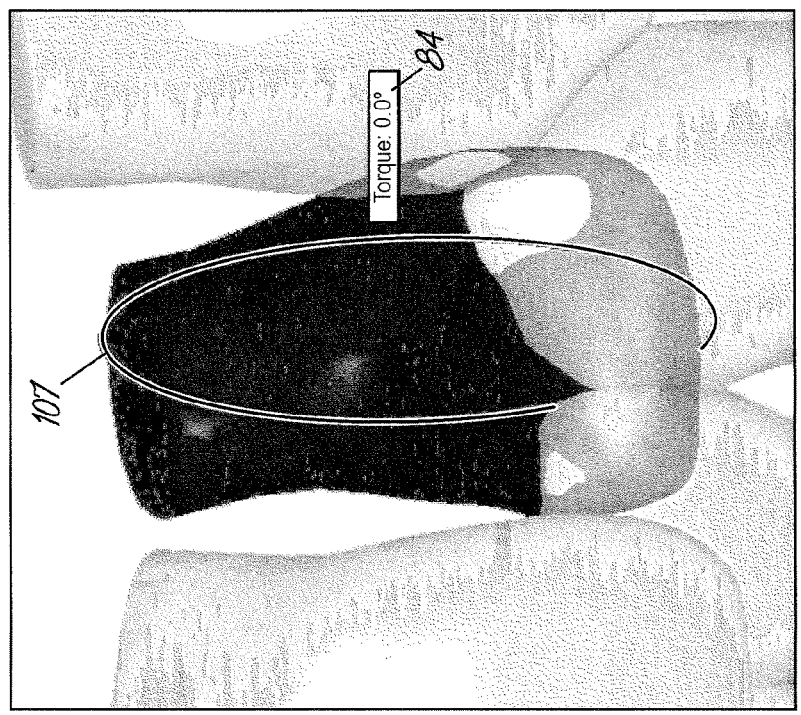
FIG. 23 contains a close up screen shot from the software showing the Torque rotational degree of freedom of movement.
Figure 22:
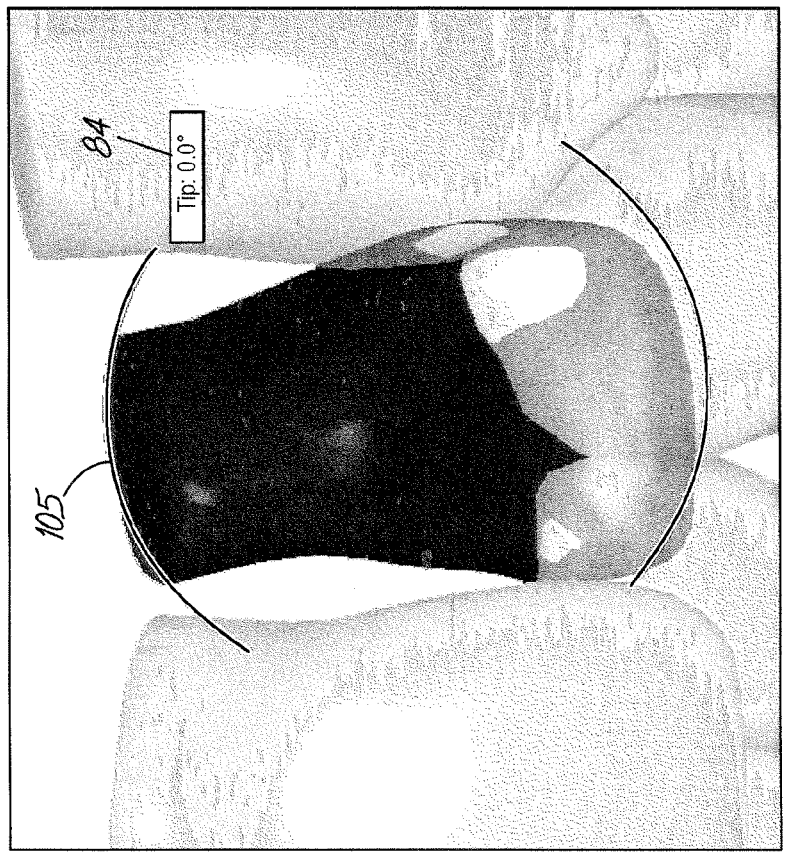
FIG. 22 contains a close up screen shot from the software showing the Tip rotational degree of freedom of movement.

Column 6, Line 6, delete "FIG. 16 contains a representative screen shot front the ...", insert --FIG. 16 contains a representative screen shot from the ...--.

Column 6, Line 37, delete "... the note is selected form the menu on the right; ...", insert --... the note is selected from the menu on the right; ...--.

Column 7, Line 23, delete "Two points on the cuspids 56 are the fixed ...", insert --Two points on the cuspids 56 are fixed ...--.

Signed and Sealed this
Twelfth Day of September, 2017

Joseph Matal
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 9,529,970 B2

Column 8, Line 5, delete "Every BC line will 64 show distance ...", insert --Every BC line 64 will show distance ...--.

Column 8, Line 6, delete "In this example 31.9 is a. BC distance ...", insert --In this example 31.9 is a BC distance ...--.

Column 8, Line 43, delete "... along with a the distance that the teeth ...", insert --... along with the distance that the teeth ...--.

Column 9, last line, delete "... helps to streamline the process for fire user and may ...", insert --... helps to streamline the process for the user and may ...--.

Column 10, Line 36, delete "... and the three rotational degrees of freedom. Rotation 103, Tip 105, and Torque 107.", insert --... and the three rotational degrees of freedom, Rotation 103, Tip 105, and Torque 107.--.

Column 10, Line 41, delete "... tool bar or from the menus, Edit and then Posted Notes,", insert --tool bar or from the menus, Edit and then Posted Notes.--.

Column 10, Line 52, delete "... either select the note based on its caption 94', 96' from the ...", insert --... either select the note based on its caption 94', 96' or from the ...--.

Column 11, Line 28, delete "Referring not to FIG. 30, the ...", insert --Referring now to FIG. 30, the ...--.

Column 12, Line 18, delete "... program as that it could be viewed as an added service ...", insert --... program as it could be viewed as an added service ...--.

In the Claims

Column 14, Line 32, Claim 14, Line 4, delete "... opposites sides of the mandible.", insert --... opposite sides of the mandible.--.

Column 14, Line 41, Claim 16, Line 3, delete "... simultaneously display an original ...", insert --... simultaneously displaying an original ...--.

Column 14, Line 47, Claim 18, Line 1, delete "The computer-implemented method of claim 8 further ...", insert --The computer-implemented method of claim 9 further ...--.